United States Patent [19]

Hasegawa et al.

[11] Patent Number: 4,876,359

[45] Date of Patent: Oct. 24, 1989

[54] NOVEL GAMMA-BUTYROLACTONE DERIVATIVES

[75] Inventors: Hiroshi Hasegawa; Noriaki Shioiri, both of Narita; Tadashi Narita, Chiba; Tatsuhiko Katori, Tone, all of Japan

[73] Assignee: SS Pharmaceutical Co., Ltd., Tokyo, Japan

[21] Appl. No.: 103,415

[22] Filed: Oct. 1, 1987

[30] Foreign Application Priority Data

Oct. 7, 1986 [JP] Japan .................................. 61-238592
Mar. 31, 1987 [JP] Japan .................................. 62-78899

[51] Int. Cl.$^4$ ........................................... C07D 207/00
[52] U.S. Cl. ..................................... 548/533; 546/245; 548/407; 548/540; 548/953; 549/265; 549/321; 549/323
[58] Field of Search ................. 549/265, 323, 321; 548/407, 540, 953, 533; 546/245

[56] References Cited

U.S. PATENT DOCUMENTS 4,310,463  1/1982  Chan ................................... 549/321
4,613,613  9/1986  Oguri et al. ....................... 549/321

FOREIGN PATENT DOCUMENTS 0090341  10/1983  European Pat. Off. .
0127090  12/1984  European Pat. Off. .
0196841  10/1985  European Pat. Off. .
0192393   8/1986  European Pat. Off. .
44-26660  11/1969  Japan .................................. 549/321
1100577   5/1986  Japan .................................. 549/321

Primary Examiner—Asok Pal
Attorney, Agent, or Firm—Oblon, Spivak, McClelland, Maier & Neustadt

[57] ABSTRACT

Novel γ-butyrolactone derivatives having strong ACE inhibitory activity are provided. They are represented by the following general formula (I):

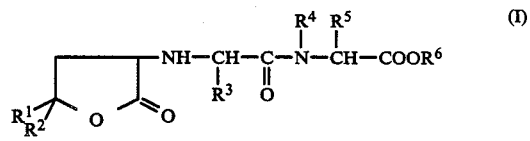

wherein $R^1$ and $R^2$ may be the same or different and mean individually a hydrogen atom or a straight-chain or branched alkyl or cycloalkyl group, or $R^1$ and $R^2$ are bonded together to mean an alkylene group having 2–6 carbon atoms, $R^3$ denotes a hydrogen atom or a lower alkyl, aralkyl, amino lower alkyl or lower alkoxycarbonylamino lower alkyl group, $R^4$ means a lower alkyl, cycloalkyl or aralkyl group, $R^5$ means a hydrogen atom or a lower alkyl group, or $R_4$ and $R_5$ are bonded together to denote an alkylene group having 2–4 carbon atoms, and $R^6$ stands for a hydrogen atom or a lower alkyl or aralkyl group; or a pharmacologically acceptable salt thereof.

3 Claims, No Drawings

NOVEL GAMMA-BUTYROLACTONE DERIVATIVES

BACKGROUND OF THE INVENTION (i) Field of the Invention

This invention relates to novel γ-butyrolactone derivatives, and more specifically to novel γ-butyrolactone derivatives useful as antihypertensive drugs.

(ii) Description of the Prior Art

It has been known that compounds, which can either inhibit or suppress the conversion of angiotensin I into angiotensin II, are useful for the treatment of hypertension. A great deal of work has hence been carried out with respect to drugs having the above converting-enzyme inhibitory effects.

The above-mentioned effects have been reported to date in regard to numerous substances. For example, Japanese Patent Laid-Open No. 218596/1986 discloses to the effect that certain specific alkylaminofuranon derivatives are useful for the treatment of hypertension. The effects of these derivatives are however still insufficient. It has therefore been desired to develop novel drugs having still better effects for hypertension.

SUMMARY OF THE INVENTION

The present inventors have synthesized a variety of γ-butyrolactone derivatives and investigated their physiological activities. In the course of the investigation, it has been found that γ-butyrolactone derivatives containing certain specific substituents have strong inhibitory effects against angiotensin converting enzymes and these compounds are useful as converting-enzyme inhibitory agents and antihypertensive agents in a wide range of applications, leading to completion of this invention.

The object of this invention is to provide a γ-butyrolactone derivative represented by the following general formula (I):

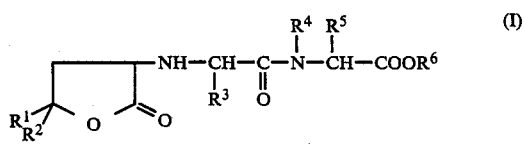

wherein $R^1$ and $R^2$ may be the same or different and mean individually a hydrogen atom or a straight-chain or branched alkyl or cycloalkyl group, or $R^1$ and $R^2$ are bonded together to mean an alkylene group having 2–6 carbon atoms, $R^3$ denotes a hydrogen atom or a lower alkyl, aralkyl, amino lower alkyl or lower alkoxycarbonylamino lower alkyl group, $R^4$ means a lower alkyl, cycloalkyl or aralkyl group, $R^5$ means a hydrogen atom or a lower alkyl group, or $R_4$ and $R_5$ are bonded together to denote an alkylene group having 2–4 carbon atoms, and $R^6$ stands for a hydrogen atom or a lower alkyl or aralkyl group; or a pharmacologically acceptable salt thereof.

Since the compounds of this invention have strong ACE inhibitory activity, they are useful for the treatment, prevention and the like of hypertension.

The above and other objects, features and advantages of the present invention will become apparent from the following description and the appended claim.

DETAILED DESCRIPTION OF THE INVENTION AND PREFERRED EMBODIMENTS

The γ-butyrolactone derivative of this invention represented by the general formula (I) can be prepared, for example, by any one of the following processes.

Process 1

In accordance with the below-described reaction scheme, a compound (IV) is obtained by reacting an amino acid (III), which has been protected as an ester, with an α-halo-γ-butyrolactone derivative (II) in the presence of a base such as tertiary amine (First Step). The protecting group of the compound (IV) is then removed to form its corresponding carboxylic acid (V) (Second Step). Further, the carboxylic acid (V) is reacted with a natural or non-natural amino acid ester derivative (VI) in the presence of a coupling reagent to obtain the intended compound (Ia) (Third Step).

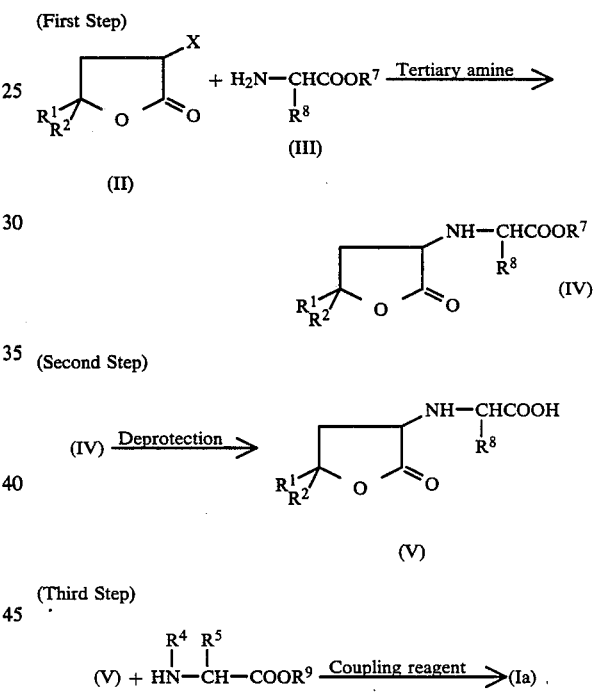

wherein $R^7$ means a pivaloyl group or a benzyl group which may contain one or more substituents, $R^8$ denotes a hydrogen atom or a lower alkyl, aralkyl or lower alkoxycarbonylamino lower alkyl group, $R^9$ is a lower alkyl or aralkyl group, X stands for a halogen atom, and $R^1$ and $R^2$ have the same meaning as defined above.

The reaction of the first step is practised by stirring the reactants at 50°–80° C., for 5–18 hours, in the presence of a tertiary amine such as triethylamine or N-methylmorpholine and in a solvent such as dimethylformamide or dimethyl sulfoxide. In the compound (II), the halogen atom amy preferably be either bromine or iodine atom.

The reaction of the second step is practised by using an anhydrous acid in accordance with the protecting group, for example, hydrochloric acid in ethyl acetate or trifluoroacetic acid in methylene chloride or by employing hydrogen gas and a catalyst, whereby the compond (V) is afforded as a free acid or an acid addition salt.

Further, the reaction of the third step is practised by a method which is followed routinely for the formation of a peptide bond. A particularly useful method includes the use of a coupling reagent such as diphenylphosphoryl azide or N,N'-dicyclohexylcarbodiimide in an aprotic solvent such as dimethylformamide, acetonitrile or ethyl acetate.

Process 2

The compound (Ib) is obtained by reacting an α-keto-γ-butyrolactone derivative (VII) and a dipeptide or its ester derivative (VIII) first under dehydrating conditions and then under reducing conditions in accordance with the following reaction formula:

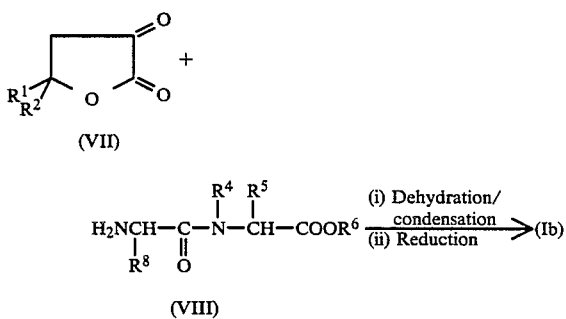

wherein $R^1$, $R^2$, $R^4$, $R^5$, $R^6$ and $R^8$ have the same meaning as defined above.

The above reaction is carried out under anhydrous conditions in an aprotonic or protonic solvent. The dehydrating and condensing reaction and reducing reaction are both practised by methods known per se in the art. A molecular sieve may be mentioned as a preferred dehydrating agent. As a preferred reducing agent on the other hand, may be mentioned hydrogen gas, which is used in combination with a catalyst, or sodium cyanoborohydride.

Process 3

The intended compound (Ic) can be obtained by reacting the ester derivative (IX) of a dipeptide with an α-halo-γ-butyrolactone derivative (II) in the presence of a base such as tertiary amine in accordance with the following reaction formula:

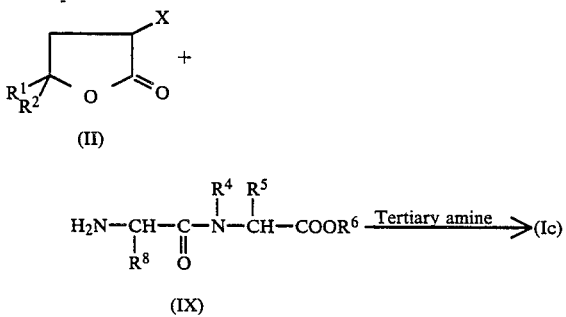

wherein $R^1$, $R^2$, $R^4$, $R^5$, $R^8$, $R^9$ and X have the same meaning as defined above.

The above reaction is carried out by stirring the reactants at 50°-80° C., for 12-48 hours, in the presence of a tertiary amine such as triethylamine or N-methylmorpholine and in a solvent such as acetonitrile or dioxane.

Where $R^3$ and $R^6$ are a lower alkoxycarbonylamino lower alkyl group and a lower alkyl or aralkyl group respectively in the compound (I) of this invention obtained by any one of such processes as described above, these substituents may be removed by a usual method so as to obtain a compound having the general formula (I) in which $R^3$ and $R^6$ are an amino lower alkyl group and a hydrogen atom respectively. As one example of such a deprotecting method, the reaction of the second step in Process 1 may be mentioned.

In addition, the compound (I) of this invention may be converted into its acid addition salts by causing various inorganic acids and organic acids to act separately thereon. Of these acid addition salts, examples of pharmacologically-preferable salts may include its inorganic and organic acid salts such as its hydrochloride, hydrobromide, sulfate, phosphate, acetate, maleate, fumarate and camphorsulfonate.

In the compound (I) of this invention obtained in the manner described above, there are asymmetric carbon atoms in its structure as indicated by asterisks (*) in the following formula (I').

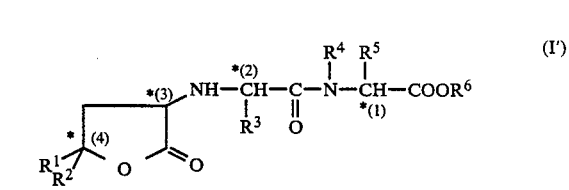

wherein $R^1$–$R^6$ have the same meaning as defined above.

There are hence various isomers owing to the inclusion of these asymmetric carbon atoms. These optical isomers, diastereomers, racemic isomers and mixtures thereof shall all be encompassed by the present invention.

As preferable isomers out of the above-mentioned isomers, may be mentioned those having S-configurations at the asymmetric carbon atoms (1) and (2).

In order to obtain such an isomer, it is necessary to use, for example, an optically active amino acid as a starting material, or to isolate the intermediate formed in each step into the corresponding isomer by a method known per se in the art, such as chromatography or fractional crystallization, and then to react the thus-isolated isomer, or to isolate the resultant compound (I) of this invention by a method known per se in the art, e.g., chromatography.

Pharmacological effects were tested with respect to certain compounds obtained in the manner described above. Results will be described next.

Angiotensin Converting Enzyme (ACE) Inhibitory Activity

The ACE inhibitory activities of the certain compounds (I) of this invention were determined by measuring their ACE activities in accordance with the method reported by Neels et al. [Clinical Chemistry, 29, 1399 (1983)].

Lyophilized powder (1 g) of rabbit lungs (product of Pel-Freez Biologicals Company) was extracted with 10 ml of a 50 mM buffer of potassium phosphate (pH 8.3) and a centrifugation supernatant (40,000 g×40 minutes) was used as an enzyme solution. Each test compound was dissolved at a concentration of 1 mg/ml in water, methanol or dimethyl sulfoxide depending on its solubility, followed by dilution with water to provide test solutions.

(Method 1)

Added to 10 μl of each of the test solutions of various concentrations was 100 μl of a mixed reactant (pH 8.3) containing 50 mM of N-2-hydroxyethylpiperazine-N'-2-ethanesulfonic acid (HEPES), 300 mM of NaCl, 400 mM of $Na_2SO_4$ and 30 mM of hippurylglycylglycine, followed by an addition of 10 μl of the enzyme solution to conduct a reaction at 37° C. for 30 minutes. To the reaction mixture, 100 μl of a sodium tungstate solution (100 g/l) and 100 μl of 0.33M sulfuric acid were added to terminate the reaction, followed by a further addition of 1 ml of water. The resultant mixture was centrifuged to collect 750 μl of a supernatant, to which 1 ml of a 100 mM borate buffer (pH 9.6) was added. Added further was 50 μl of a 60 mM solution of sodium 2,4,6-tri-nitrobenzenesulfonate. After warming the mixture at 37° C. for 15 minutes, its absorbance was measured at 420 nm. The inhibition rates at the various concentrations were calculated and $IC_{50}$ was then determined by a method known per se in the art. Results are summarized in Table 1.

TABLE 1

| | ACE Inhibitory Activity |
|---|---|
| Compound No.* | ACE inhibitory activity concentration ($IC_{50}$; M) |
| 14 | $7.0 \times 10^{-9}$ |
| 19 | $7.3 \times 10^{-9}$ |
| 20 | $5.8 \times 10^{-9}$ |
| 21 | $2.9 \times 10^{-9}$ |
| 22 | $3.0 \times 10^{-9}$ |
| Comparative** compound | $1.4 \times 10^{-8}$ |

*Identical to those described in the Examples of the corresponding numbers. All the compounds are in the form of their hydrochlorides.
**Comparative compound:

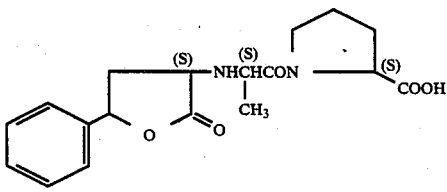

(Japanese Patent Laid-Open No. 218596/1986)

As apparent from Table 1, the compounds according to this invention shows strong ACE inhibitory activity.

(Method 2)

Mixed to 1800 μl of rat plasma was 200 μl of each test solution, followed by incubation at 37° C. for 1 hour. The resulting mixture was then diluted with a 0.1M Tris-HCl buffer (pH 8.3). The procedure of Method 1 was thereafter followed to measure the ACE inhibitory activity. Results are shown in Table 2.

TABLE 2

| | ACE Inhibitory Activity |
|---|---|
| Compound No.* | ACE inhibitory activity concentration ($IC_{50}$; M) |
| 35 | $4.7 \times 10^{-9}$ |
| 37 | $5.7 \times 10^{-9}$ |
| 38 | $4.0 \times 10^{-9}$ |

*Identical to those described in the Examples of the corresponding numbers. All the compounds are in the form of their dihydrochlorides.

As apparent from Table 2, the compounds according to this invention shows strong ACE inhibitory activity.

Having generally described the invention, a more complete understanding can be obtained by reference to certain specific examples, which are provided herein for purposes of illustration only and are not intended to be limiting unless otherwise specified.

EXAMPLES

The present invention will hereinafter be described by the following Examples.

Example 1

(1) Dissolved in 100 ml of dimethylformamide were 18.45 g of L-alanine benzyl ester p-toluene-sulfonate and 13.86 g of 2-bromo-4-octyl-γ-butyrolactone. After a dropwise addition of 10.1 g of triethylamine, the resultant mixture was heated and stirred at 70° C. for 9 hours. The reaction mixture was poured into chilled water, followed by extraction with ethyl acetate. The extract was washed successively with water, a 2% aqueous solution of sodium hydrogencarbonate, and water. After drying the extract over anhydrous sodium sulfate, it was distilled under reduced pressure to obtain 18.0 g of a pale-yellow oily substance. N-(2-oxo-5-octyl-3-tetrahydrofuranyl)-L-alanine benzyl ester was contained in the oily substance. As a result of an analysis by high-performance liquid chromatography, it was a mixture of four diastereomers.

The pale-yellow oily substance (9.0 g) was then isolated and purified by chromatography on a silica gel column (toluene:ethyl acetate=50:1–10:1). From initial fractions of the column effluent, 2.32 g of a diastereomer of N-(2-oxo-5-octyl-3-tetrahydrofuranyl)-L-alanine benzyl ester (this compound and its corresponding isomers wil lhereinafter be called Isomer A) was obtained as a colorless oily substance.

IR $\nu_{max}^{neat}$cm$^{-1}$: 3320, 1775, 1735.

$^1$H-NMR δppm(CDCl$_3$): 7.33 (s, 5H), 5.14 (s, 2H), 4.19 (m, 1H), 3.51 (d.d, 1H), 3.41 (d.d, 1H), 2.47 (m, 1H), 1.81–1.10 (m, 15H), 1.33 (d, 3H), 0.86 (t, 3H).

Mass (EI) m/z: 375 (M$^+$). [α]$_D$: −36.0° (C=1, methanol).

From subsequent fractions of the column effluent, 4.63 g of other diasteromers of N-(2-oxo-5-octyl-3-tetrahydrofuranyl)-L-alanine benzyl ester (this compound and its corresponding isomers will hereinafter called "Isomer BCD") was obtained as a colorless oily substance.

IR $\nu_{max}^{neat}$cm$^{-1}$: 3320, 1775, 1735.

$^1$H-NMR δ ppm(CDCl$_3$): 7.33(s, 5H), 5.14(s, 2H), 4.65–4.04(m, 1H), 3.91–3.32(m, 2H), 2.55–1.98(m, 1H), 1.80–1.08(m, 18H), 0.86(t, 3H).

Mass(EI) m/z: 375(M$^+$).

[α]$_D$: −7.8° (C=1, methanol).

(2) Dissolved in 100 ml of methanol was 3.75 g of Isomer BCD of N-(2-oxo-5-octyl-3-tetrahydrofuranyl)-L-alanine benzyl ester. Thereafer, 0.70 g of 10% palladium-charcoal was added and the reaction mixture was hydrogenated at room temperature and normal pressure for 2 hours. The palladium-charcoal was then filtered off and the filtrate was distilled under reduced pressure to obtain crystals. The crystals were recrystallized from methanol, thereby obtaining 2.41 g of Isomer BCD of N-(2-oxo-5-octyl-3-tetrahydrofuranyl)-L-alanine as colorless crystals.

Melting point: 182°–185° C.

IR $\nu_{max}^{KBr}$ cm$^{-1}$: 1775, 1595.

¹H-NMR δ ppm(DMSO-d₆): 4.64–4.13(m, 1H), 3.74–3.20(m, 2H), 2.06(t.d, 1H), 1.74–1.10 (m, 18H), 0.85(t, 3H).

Mass(FAB) m/z: 286[(M+H)⁺].

(3) Dissolved in 30 ml of dimethylformamide were 2.28 g of Isomer BCD of N-(2-oxo-5-octyl-3-tetrahydrofuranyl)-L-alanine and 2.13 g of L-proline benzyl ester hydrochloride. N-methylmorpholine (0.89 g) was added dropwise at 0° C. under stirring. Five minutes later, 1.98 g of diphenylphosphoryl azide was added and 1.21 g of N-methylmorpholine was then added dropwise again. After completion of the dropwise addition, the reaction mixture was stirred at 0° C. for 1 hour, followed by further stirring at room temperature for 18 hours. The reaction mixture was poured into chilled water, followed by extraction with ethyl acetate. The extract was washed successively with water, a 2% aqueous solution of sodium hydrogen-carbonate and water. After drying the extract over anhydrous sodium sulfate, it was distilled under reduced pressure. The residue was isolated and purified by chromatography on a silica gel column (chloroform:ethyl acetate=10:1–10:3). From initial fractions of the column effluent, 2.28 g of a diastereomer of N-(2-oxo-5-octyl-3-tetrahydrofuranyl)-L-alanyl-L-proline benzyl ester (this compound and its corresponding isomers will hereinafter be called Isomer B) was obtained as a colorless syrupy substance [In the formula (I), $R^1$=—(CH₂)₇CH₃, $R^2$=H, $R^3$=CH₃, $R^4$ and $R^5$=—(CH₂)₃—, $R^6$=—CH₂Ph (Compound 1)].

IR $\nu_{max}^{neat}$ cm⁻¹: 3330, 1770, 1740, 1640.

¹H-NMR δ ppm(CDCl₃): 7.32(s, 5H), 5.20(d, 1H), 5.03(d, 1H), 4.65–3.97(m, 2H), 3.90–3.17(m, 4H), 2.66–1.08(m, 23H), 0.86(t, 3H).

Mass(EI) m/z: 472(M⁺).

$[\alpha]_D$: −91.6° (C=1, methanol).

From still subsequent fractions of the column effluent, 0.52 g of a mixture of diastereomers (this compound and its corresponding isomers will hereinafter called "Isomer CD") was obtained as a colorless syrupy substance.

IR $\nu_{max}^{neat}$ cm⁻¹: 3310, 1770, 1745, 1640.

¹H-NMR δ ppm(CDCl₃): 7.31(s, 5H), 5.20(d, 1H), 5.03(d, 1H), 4.68–3.96(m, 2H), 3.84–3.14(m, 4H), 2.44–1.08(m, 23H), 0.86(t, 3H).

Mass(EI) m/z: 472(M⁺).

$[\alpha]_D$: −25.2° (C=1, methanol).

Examples 2–11

Compounds given below in Examples 2–11 were obtained by using their corresponding 2-halo-4-alkyl-γ-butyrolactones and conducting Steps (1), (2) and (3) of Example 1.

(Example 2)

(1) N-(2-oxo-5-methyl-3-tetrahydrofuranyl)-L-alanine benzyl ester (Isomer BCD)

Appearance: Colorless oily substance.
IR $\nu_{max}^{neat}$ cm⁻¹: 3320, 1775, 1735.

(2) N-(2-oxo-5-methyl-3-tetrahydrofuranyl)-L-alanine (Isomer BCD):

Appearance: Colorless crystals.
Melting point: 194°–197° C.
IR $\nu_{max}^{KBr}$ cm⁻¹: 1795, 1610.

(3) N-(2-oxo-5-methyl-3-tetrahydrofuranyl)-L-alanyl-L-proline benzyl ester (Isomer B) [in the formula (I), $R^1$=CH₃, $R^2$=H, $R^3$=CH₃, $R^4$ and $R^5$=—(CH₂)₃—, $R^6$=—CH₂Ph (Compound 2)]:

Appearance: Colorless syrupy substance.
IR $\nu_{max}^{neat}$ cm⁻¹: 3320, 1770, 1745, 1645.
¹H-NMR δ ppm(CDCl₃): 7.31(s, 5H), 5.20(d, 1H), 5.03(d, 1H), 4.62–3.96(m, 2H), 3.90–3.17(m, 4H), 2.68–1.56(m, 6H), 1.39(d, 3H), 1.21(d, 3H).
Mass(EI) m/z: 374(M⁺).
$[\alpha]_D$: −96.7° (C=1, methanol).

(Example 3)

(1) N-(2-oxo-5-ethyl-3-tetrahydrofuranyl)-L-alanine benzyl ester (Isomer BCD):

Appearance: Colorless oily substance.
IR $\nu_{max}^{neat}$ cm⁻¹: 3330, 1775, 1735.

(2) N-(2-oxo-5-ethyl-3-tetrahydrofuranyl)-L-alanine (Isomer BCD):

Appearance: Colorless crystals.
Melting point: 207°–209° C.
IR $\nu_{max}^{KBr}$ cm⁻¹: 1795, 1610.

(3) N-(2-oxo-5-ethyl-3-tetrahydrofuranyl)-L-alanyl-L-proline benzyl ester (Isomer B) [in the formula (I), $R^1$=—CH₂CH₃, $R^2$=H, $R^3$=CH₃, $R^4$ and $R^5$=—(CH₂)₃—, $R^6$=—CH₂Ph (Compound 3)]:

Appearance: Colorless syrupy substance.
IR $\nu_{max}^{neat}$ cm⁻¹: 3310, 1770, 1740, 1640.
¹H-NMR δ ppm(CDCl₃): 7.31(s, 5H), 5.21(d, 1H), 5.03(d, 1H), 4.65–3.95(m, 2H), 3.90–3.17(m, 4H), 2.65–1.46(m, 8H), 1.22(d, 3H), 0.96(t, 3H).
Mass(EI) m/z: 388(M⁺).
$[\alpha]_D$: −97.3° (C=1, methanol).

(Example 4)

(1) N-(2-oxo-5-propyl-3-tetrahydrofuranyl)-L-alanine benzyl ester (Isomer BCD):

Appearance: Colorless oily substance.
IR $\nu_{max}^{neat}$ cm⁻¹: 3320, 1770, 1730.

(2) N-(2-oxo-5-propyl-3-tetrahydrofuranyl)-L-alanine (Isomer BCD):

Appearance: Colorless crystals.
Melting point: 197°–199° C.
IR $\nu_{max}^{KBr}$ cm⁻¹: 1775, 1590.

(3) N-(2-oxo-5-propyl-3-tetrahydrofuranyl)-L-alanyl-L-proline benzyl ester (Isomer B) [in the formula (I), $R^1$=—(CH₂)₂CH₃, $R^2$=H, $R^3$=CH₃, $R^4$ and $R^5$=—(CH₂)₃—, $R^6$=—CH₂Ph (Compound 4)]:

Appearance: Colorless syrupy substance.
IR $\nu_{max}^{neat}$ cm⁻¹: 3310, 1770, 1745, 1645.
¹H-NMR δ ppm(CDCl₃): 7.31(s, 5H), 5.20(d, 1H), 5.03(d, 1H), 4.66–3.96(m, 2H), 3.91–3.16(m, 4H), 2.65–1.30(m, 10H), 1.23(d, 3H), 0.92(t, 3H).
Mass(EI) m/z: 402(M⁺).
$[\alpha]_D$: −87.8° (C=1, methanol).

(Example 5)

(1) N-(2-oxo-5-butyl-3-tetrahydrofuranyl)-L-alanine benzyl ester (Isomer BCD):

Appearance: Colorless oily substance.
IR $\nu_{max}^{neat}$ cm⁻¹: 3330, 1775, 1735.

(2) N-(2-oxo-5-butyl-3-tetrahydrofuranyl)-L-alanine (Isomer BCD):

Appearance: Colorless crystals.
Melting point: 182°–185° C.
IR $\nu_{max}^{KBr}$ cm⁻¹: 1770, 1590.

(3) N-(2-oxo-5-butyl-3-tetrahydrofuranyl)-L-alanyl-L-proline benzyl ester (Isomer B) [in the formula (I), $R^1$=—(CH₂)₃CH₃, $R^2$=H, $R^3$=CH₃, $R^4$ and $R^5$=—(CH₂)₃—, $R^6$=—CH₂Ph (Compound 5)]:

Appearance: Colorless syrupy substance.
IR $\nu_{max}^{neat}$ cm$^{-1}$: 3310, 1770, 1745, 1640.
$^1$H-NMR δ ppm(CDCl$_3$): 7.31(s, 5H), 5.21(d, 1H), 5.03(d, 1H), 4.65-3.98(m, 2H), 3.90-3.18(m, 4H), 2.66-1.20(m, 12H), 1.23(d, 3H), 0.88(t, 3H).
Mass(EI) m/z: 416(M$^+$).
$[\alpha]_D$: −100.3° (C=1, methanol).

(Example 6)

(1) N-(2-oxo-5-pentyl-3-tetrahydrofuranyl)-L-alanine benzyl ester (Isomer BCD):
Appearance: Colorless oily substance.
IR $\nu_{max}^{neat}$ cm$^{-1}$: 3320, 1775, 1735.
(2) N-(2-oxo-5-pentyl-3-tetrahydrofuranyl)-L-alanine (Isomer BCD):
Appearance: Colorless crystals.
Melting point: 184°-186° C.
IR $\nu_{max}^{KBr}$ cm$^{-1}$: 1770, 1590.
(3) N-(2-oxo-5-pentyl-3-tetrahydrofuranyl)-L-alanyl-L-proline benzyl ester (Isomer B) [in the formula (I), R$^1$=—(CH$_2$)$_4$CH$_3$, R$^2$=H, R$^3$=CH$_3$, R$^4$ and R$^5$=—(CH$_2$)$_3$—, R$^6$=—CH$_2$Ph (Compound 6)]:
Appearance: Colorless syrupy substance.
IR $\nu_{max}^{neat}$ cm$^{-1}$: 3310, 1770, 1745, 1640.
$^1$H-NMR δ ppm(CDCl$_3$): 7.32(s, 5H), 5.21(d, 1H), 5.04(d, 1H), 4.67-3.98(m, 2H), 3.90-3.19(m, 4H), 2.67-1.15(m, 14H), 1.24(d, 3H), 0.87(t, 3H).
Mass(EI) m/z: 430(M$^+$).
$[\alpha]_D$: −92.8° (C=1, methanol).

(Example 7)

(1) N-(2-oxo-5-hexyl-3-tetrahydrofuranyl)-L-alanine benzyl ester (Isomer BCD):
Appearance: Colorless oily substance.
IR $\nu_{max}^{neat}$ cm$^{-1}$: 3320, 1775, 1735.
(2) N-(2-oxo-5-hexyl-3-tetrahydrofuranyl)-L-alanine (Isomer BCD):
Appearance: Colorless crystals.
Melting point: 173°-177° C.
IR $\nu_{max}^{KBr}$ cm$^{-1}$: 1775, 1595.
(3) N-(2-oxo-5-hexyl-3-tetrahydrofuranyl)-L-alanyl-L-proline benzyl ester (Isomer B) [in the formula (I), R$^1$=—(CH$_2$)$_5$CH$_3$, R$^2$=H, R$^3$=CH$_3$, R$^4$ and R$^5$=—(CH$_2$)$_3$—, R$^6$=—CH$_2$Ph (Compound 7)]:
Appearance: Colorless syrupy substance.
IR $\nu_{max}^{neat}$ cm$^{-1}$: 3320, 1770, 1745, 1640.
$^1$H-NMR δ ppm(CDCl$_3$): 7.31(s, 5H), 5.21(d, 1H), 5.04(d, 1H), 4.65-3.98(m, 2H), 3.90-3.18(m, 4H), 2.66-1.10(m, 19H), 0.87(t, 3H).
Mass(EI) m/z: 444(M$^+$).
$[\alpha]_D$: −98.5° (C=1, methanol).

(Example 8)

(1) N-(2-oxo-5-heptyl-3-tetrahydrofuranyl)-L-alanine benzyl ester (Isomer BCD):
Appearance: Colorless oily substance.
IR $\nu_{max}^{neat}$ cm$^{-1}$: 3320, 1775, 1735.
(2) N-(2-oxo-5-heptyl-3-tetrahydrofuranyl)-L-alanine (Isomer BCD):
Appearance: Colorless crystals.
Melting point: 167°-170° C.
IR $\nu_{max}^{KBr}$ cm$^{-1}$: 1775, 1590.
(3) N-(2-oxo-5-heptyl-3-tetrahydrofuranyl)-L-alanyl-L-proline benzyl ester (Isomer B) [in the formula (I), R$^1$=—(CH$_2$)$_6$CH$_3$, R$^2$=H, R$^3$=CH$_3$, R$^4$ and R$^5$=—(CH$_2$)$_3$—, R$^6$=—CH$_2$Ph (Compound 8)]:
Appearance: Colorless syrupy substance.
IR $\nu_{max}^{neat}$ cm$^{-1}$: 3320, 1770, 1740, 1640.
$^1$H-NMR δ ppm(CDCl$_3$): 7.32(s, 5H), 5.21(d, 1H), 5.04(d, 1H), 4.65-3.99(m, 2H), 3.89-3.19(m, 4H), 2.67-1.10(m, 21H), 0.87(t, 3H).
Mass(EI) m/z: 458(M$^+$).
$[\alpha]_D$: −88.4° (C=1, methanol).

(Example 9)

(1) N-(2-oxo-5-decanyl-3-tetrahydrofuranyl)-L-alanine benzyl ester (Isomer BCD):
Appearance: Colorless oily substance.
IR $\nu_{max}^{neat}$ cm$^{-1}$: 3330, 1780, 1735.
(2) N-(2-oxo-5-decanyl-3-tetrahydrofuranyl)-L-alanine (Isomer BCD):
Appearance: Colorless crystals.
Melting point: 172°-174° C.
IR $\nu_{max}^{KBr}$ cm$^{-1}$: 1775, 1590.
(3) N-(2-oxo-5-decanyl-3-tetrahydrofuranyl)-L-alanyl-L-proline benzyl ester (Isomer B) [in the formula (I), R$^1$=—(CH$_2$)$_9$CH$_3$, R$^2$=H, R$^3$=CH$_3$, R$^4$ and R$^5$=—(CH$_2$)$_3$—, R$^6$=—CH$_2$Ph (Compound 9)]:
Appearance: Colorless syrupy substance.
IR $\nu_{max}^{neat}$ cm$^{-1}$: 3330, 1770, 1745, 1635.
$^1$H-NMR δ ppm(CDCl$_3$): 7.32(s, 5H), 5.21(d, 1H), 5.03(d, 1H), 4.67-3.97(m, 2H), 3.90-3.17(m, 4H), 2.66-1.00(m, 27H), 0.86(t, 3H).
Mass(EI) m/z: 500(M$^+$).
$[\alpha]_D$: −78.9° (C=1, methanol).

(Example 10)

(1) N-(2-oxo-5-dodecanyl-3-tetrahydrofuranyl)-L-alanine benzyl ester (Isomer BCD):
Appearance: Colorless oily substance.
IR $\nu_{max}^{neat}$ cm$^{-1}$: 3330, 1780, 1735.
(2) N-(2-oxo-5-dodecanyl-3-tetrahydrofuranyl)-L-alanine (Isomer BCD):
Appearance: Colorless crystals.
Melting point: 183°-185° C.
(3) N-(2-oxo-5-dodecanyl-3-tetrahydrofuranyl)-L-alanyl-L-proline benzyl ester (Isomer B) [in the formula (I), R$^1$=—(CH$_2$)$_{11}$CH$_3$, R$^2$=H, R$^3$=CH$_3$, R$^4$ and R$^5$=—(CH$_2$)$_3$—, R$^6$=—CH$_2$Ph (Compound 10)]:
Appearance: Colorless syrupy substance.
IR $\nu_{max}^{neat}$ cm$^{-1}$: 3330, 1770, 1740, 1635.
$^1$H-NMR δ ppm(CDCl$_3$): 7.31(s, 5H), 5.20(d, 1H), 5.03(d, 1H), 4.67-3.97(m, 2H), 3.90-3.16(m, 4H), 2.65-1.00(m, 31H), 0.86(t, 3H).
Mass(EI) m/z: 528(M$^+$).
$[\alpha]_D$: −64.2° (C=1, methanol).

(Example 11)

(1) N-(2-oxo-5-tetradecanyl-3-tetrahydrofuranyl)-L-alanine benzyl ester (Isomer BCD):
Appearance: Colorless oily substance.
IR $\nu_{max}^{KBr}$ cm$^{-1}$: 3320, 1775, 1735.
(2) N-(2-oxo-5-tetradecanyl-3-tetrahydrofuranyl)-L-alanine (Isomer BCD):
Appearance: Colorless crystals.
Melting point: 182°-184° C.
IR $\nu_{max}^{KBr}$ cm$^{-1}$: 1775, 1590.
(3) N-(2-oxo-5-tetradecanyl-3-tetrahydrofuranyl)-L-alanyl-L-proline benzyl ester (Isomer B) [in the formula (I), R$^1$=—(CH$_2$)$_{13}$CH$_3$, R$^2$=H, R$^3$=CH$_3$, R$^4$ and R$^5$=—(CH$_2$)$_3$—, R$^6$=—CH$_2$Ph (Compound 11)]:
Appearance: Colorless syrupy substance.
IR $\nu_{max}^{neat}$ cm$^{-1}$: 3320, 1770, 1740, 1635.
$^1$H-NMR δ ppm (CDCl$_3$): 7.30(s, 5H), 5.20(d, 1H), 5.03(d, 1H), 4.64-3.96(m, 2H), 3.88-3.17(m, 4H), 2.64-1.00(m, 35H), 0.86(t, 3H).

Mass(EI) m/z: 556(M+).

$[\alpha]_D$: −75.0° (C=1, methanol).

Example 12

(1) Dissolved in 40 ml of dimethylformamide were 8.54 g of L-phenylalanine benzyl ester p-toluenesulfonate and 3.40 g of 2-bromo-γ-butyrolactone. After a dropwise addition of 4.04 g of triethylamine, the resultant mixture was heated and stirred at 70° C. for 18 hours. The reaction mixture was poured into chilled water, followed by extraction with ethyl acetate. The extract was washed successively with water, a 2% aqueous solution of sodium hydrogencarbonate, and water. After drying the extract over anhydrous sodium sulfate, it was distilled under reduced pressure. The residue was isolated and purified by chromatography on a silica gel column (toluene:ethyl acetate=20:1–5:1). From initial fractions of the column effluent, 1.75 g of N-(2-oxo-3-tetrahydrofuranyl)-L-phenylalanine benzyl ester (Isomer A) was obtained as a colorless oily substance.

IR $\nu_{max}^{neat}$ cm$^{-1}$: 3330, 1780, 1740.

$^1$H-NMR δ ppm(CDCl$_3$): 7.30(m, 5H), 7.19(m, 5H), 5.08(s, 2H), 4.41–4.01(m, 2H), 3.57(t, 1H), 3.43(d.d, 1H), 2.95(d, 2H), 2.50–1.76(m, 2H).

Mass(EI) m/z: 339(M+).

$[\alpha]_D$: −2.9° (C=1, ethanol).

From subsequent fractions of the column effluent, 2.16 g of N-(2-oxo-3-tetrahydrofuranyl)-L-phenylalanine benzyl ester (Isomer B) was obtained as colorless crystals.

Melting point: 46°–47° C.

IR $\nu_{max}^{KBr}$ cm$^{-1}$: 3330, 1780, 1735.

$^1$H-NMR δ ppm(CDCl$_3$): 7.30(m, 5H), 7.19(m, 5H), 5.07(s, 2H), 4.41–3.92(m, 3H), 3.46(d.d, 1H), 2.99(d, 2H), 2.50–1.82(m, 2H).

Mass(EI) m/z: 339(M+).

$[\alpha]_D$: −21.0° (C=1, ethanol).

(2) Using N-(2-oxo-3-tetrahydrofuranyl)-L-phenylalanine benzyl ester (Isomer B), a reaction and treatments similar to those performed in Step (2) of Example 1 were conducted to obtain N-(2-oxo-3-tetrahyrofuranyl)-L-phenylalanine (Isomer B) as colorless crystals.

Melting point: 164°–165° C.

IR $\nu_{max}^{KBr}$ cm$^{-1}$: 1795, 1620.

$^1$H-NMR δ ppm(DMSO-d$_6$): 7.22(s, 5H), 4.16(m, 2H), 3.65(d.d, 1H), 3.62(d.d, 1H), 2.86(d, 2H), 2.50–1.71(m, 2H).

Mass(FAB) m/z: 250[(M+H)+].

(3) Conducting a reaction and treatments in the same manner as in Step (3) of Example 1 except for the use of N-(2-oxo-3-tetrahydrofuranyl)-L-phenylalanine (Isomer B) instead of Isomer BCD of N-(2-oxo-5-octyl-3-tetrahydrofuranyl)-L-analine, was obtained as a colorless syrupy substance N-(2-oxo-3-tetrahydrofuranyl)-L-phenylalanyl-L-proline benzyl ester (Isomer B) [in the formula (I), R$^1$=R$^2$=H, R$^3$=—CH$_2$Ph, R$^4$ and R$^5$=—(CH$_2$)$_3$—, R$^6$=—CH$_2$Ph (Compound 12)].

IR $\nu_{max}^{neat}$ cm$^{-1}$: 3320, 1780, 1740, 1645.

$^1$H-NMR δ ppm(CDCl$_3$): 7.32(b.s, 5H), 7.23(b.s, 5H), 5.12(d, 2H), 4.62–3.89(m, 4H), 3.75–2.68(m, 5H), 2.56–1.50(m, 6H).

Mass(EI) m/z: 436(M+).

$[\alpha]_D$: −67.3° (C=1, ethanol).

Example 13

(1) Dissolved in 30 ml of dimethylformamide were 2.54 g of L-alanine t-butyl ester hydrochloride and 2.38 g of 2-bromo-γ-butyrolactone. After a dropwise addition of 2.83 g of triethylamine, the resultant mixture was heated and stirred at 70° C. for 5 hours. The reaction mixture was poured into chilled water, followed by extraction with ethyl acetate. The extract was washed successivley with water, a 2% aqueous solution of sodium hydrogencarbonate, and water. After drying the extract over anhydrous sodium sulfate, it was distilled under reduced pressure. The residue was isolated and purified by chromatography on a silica gel column (toluene:ethyl acetate=20:1), thereby obtaining 1.86 g of N-(2-oxo-3-tetrahydrofuranyl)-L-alanine t-butyl ester as a colorless oily substance.

IR $\nu_{max}^{neat}$ cm$^{-1}$: 3320, 1780, 1730.

(2) In 5 ml of an ethyl acetate solution saturated with hydrochloric acid, 1.66 g of N-(2-oxo-3-tetrahydrofuranyl)-L-alanine t-butyl ester was dissolved. The resultant solution was stirred for 3 hours at room temperature. Crystals which had precipitated were collected by filtration. After washing the crystals with ethyl acetate and then with ether, they were dried to obtain 1.31 g of N-(2-oxo-3-tetrahydrofuranyl)-L-alanine hydrochloride as colorless crystals.

Melting point: 196°–200° C.

IR $\nu_{max}^{KBr}$ cm$^{-1}$: 3430, 1785.

(3) Conducting a reaction and treatments in the same manner as in Step (3) of Example 1 except that N-(2-oxo-3-tetrahydrofuranyl)-L-alanine hydrochloride was used in a form neutralized with N-methylmorpholine in place of Isomer BCD of N-(2-oxo-5-octyl-3-tetrahydrofuranyl)-L-alanine, was obtained as a colorless syrupy substance N-(2-oxo-3-tetrahydrofuranyl)-L-alanyl-L-proline benzyl ester [in the formula (I), R$^1$=R$^2$=H, R$^3$=CH$_3$, R$^4$ and R$^5$=—(CH$_2$)$_3$—, R$^6$=—CH$_2$Ph (Compound 13)].

IR $\nu_{max}^{neat}$ cm$^{-1}$: 3330, 1775, 1745, 1645.

$^1$H-NMR δ ppm(CDCl$_3$): 7.31(s, 5H), 5.21(d, 1H), 5.03(d, 1H), 4.67–3.95(m, 3H), 3.80–3.18(m, 4H), 2.54–1.72(m, 6H), 1.21(d, 3H).

Mass(EI) m/z: 360(M+).

Example 14

Dissolved in 50 ml of methanol was 3.80 g of Isomer B of N-(2-oxo-5-hexyl-3-tetrahydrofuranyl)-L-alanyl-L-proline benzyl ester (Compound 7). Thereafter, 0.40 g of 10% palladium-charcoal was added and the reaction mixture was hydrogenated at room temperature and normal pressure for 2 hours. The palladium-charcoal was then filtered off and the filtrate was distilled under reduced pressure to obtain as white powder 2.80 g of N-(2-oxo-5-hexyl-3-tetrahydrofuranyl)-L-alanyl-L-proline (Isomer B) [in the formula (I), R$^1$=—(CH$_2$)$_5$CH$_3$, R$^2$=H, R$^3$=CH$_3$, R$^4$ and R$^5$=—(CH$_2$)$_3$—, R$^6$=H (Compound 14)].

Dissolved in 10 ml of ethyl acetate was 1.40 g of the white powder, followed by a dropwise addition of an ethyl acetate solution saturated with hydrochloric acid. The dropwise addtion was continued until no additional crystals precipitated. Crystals thus precipitated were collected by filtration. After washing the crystals with ethyl acetate and then with ether, they were dried to obtain 1.31 g of the hydrochloride of Compound 14 as colorless crystals.

Melting point: 183°–185° C.

IR $\nu_{max}^{KBr}$cm$^{-1}$: 1775, 1710, 1640.
$^1$H-NMR δ ppm(DMSO-d$_6$): 4.74–4.05(m, 4H), 3.57(m, 2H), 2.76–1.12(m, 16H), 1.44(d, 3H), 0.85(t, 3H).
Mass(FAB) m/z: 355[(M+H-HCl)$^+$].
[α]$_D$: −77.0° (C=1, methanol).

Examples 15–26

Conducting a reaction and treatments in the same manner as in Example 14 except for the separate use of Compounds 1–6 and 8–13 instead of Compound 7, the hydrochlorides of compounds given below in Examples 15–26 were each obtained as colorless crystals.

(Example 15)

Hydrochloride of N-(2-oxo-5-methyl-3-tetrahydrofuranyl)-L-alanyl-L-proline (Isomer B) [in the formula (I), R$^1$=CH$_3$, R$^2$=H, R$^3$=CH$_3$, R$^4$ and R$^5$=—(CH$_2$)$_3$—, R$^6$=H (Compound 15)]:
Melting point: 159°–162° C.
IR $\nu_{max}^{KBr}$cm$^{-1}$: 1775, 1730, 1645.
$^1$H-NMR δ ppm(DMSO-d$_6$): 4.70–4.09(m, 4H), 3.57(m, 2H), 2.75–1.79(m, 6H), 1.42(d, 3H), 1.25(d, 3H).
Mass(FAB) m/z: 285[(M+H-HCl)$^+$].
[α]$_D$: −87.5° (C=1, methanol).

(Example 16)

Hydrochloride of N-(2-oxo-5-ethyl-3-tetrahydrofurnayl)-L-alanyl-L-proline (Isomer B) [in the formula (I), R$^1$=CH$_2$CH$_3$, R$^2$=H, R$^3$=CH$_3$, R$^4$ and R$^5$=—(CH$_2$)$_3$—, R$^6$=H (Compound 16)]:
Melting point: 142°–144° C.
IR $\nu_{max}^{KBr}$cm$^{-1}$: 1780, 1730, 1650.
$^1$H-NMR δ ppm(DMSO-d$_6$): 4.70–4.05(m, 4H), 3.57(m, 2H), 2.75–1.70(m, 8H), 1.43(d, 3H), 0.91(t, 3H).
Mass(FAB) m/z: 299[(M+H-HCl)$^+$].
[α]$_D$: −82.0° (C=1, methanol).

(Example 17)

Hydrochloride of N-(2-oxo-5-propyl-3-tetrahydrofuranyl)-L-alanyl-L-proline (Isomer B) [in the formula (I), R$^1$=—(CH$_2$)$_2$CH$_3$, R$^2$=H, R$^3$=CH$_3$, R$^4$ and R$^5$=—(CH$_2$)$_3$—, R$^6$=H (Compound 17)]:
Melting point: 169°–171° C.
IR $\nu_{max}^{KBr}$cm$^{-1}$: 1780, 1730, 1650.
$^1$H-NMR δ ppm(DMSO-d$_6$): 4.77–4.06(m, 4H), 3.58(m, 2H), 2.78–1.25(m, 10H), 1.45(d, 3H), 0.92(t, 3H).
Mass(FAB) m/z: 313[(M+H-HCl)$^+$].
[α]$_D$: −82.4° (C=1, methanol).

(Example 18)

Hydrochloride of N-(2-oxo-5-butyl-3-tetrahydrofuranyl)-L-alanyl-L-proline (Isomer B) [in the formula (I), R$^1$=—(CH$_2$)$_3$CH$_3$, R$^2$=H, R$^3$=CH$_3$, R$^4$ and R$^5$=—(CH$_2$)$_3$—, R$^6$=H (Compound 18)]:
Melting point: 178°–180° C.
IR $\nu_{max}^{KBr}$cm$^{-1}$: 1780, 1730, 1645.
$^1$H-NMR δ ppm(DMSO-d$_6$): 4.74–4.05(m, 4H), 3.59(m, 2H), 2.79–1.18(m, 12H), 1.48(d, 3H), 0.90(t, 3H).
Mass(FAB) m/z: 327[(M+H-HCl)$^+$].
[α]$_D$: −82.8° (C=1, methanol).

(Example 19)

Hydrochloride of N-(2-oxo-5-pentyl-3-tetrahydrofuranyl)-L-alanyl-L-proline (Isomer B) [in the formula (I), R$^1$=—(CH$_2$)$_4$CH$_3$, R$^2$=H, R$^3$=CH$_3$, R$^4$ and R$^5$=—(CH$_2$)$_3$—, R$^6$=H (Compound 19)]:
Melting point: 168°–170° C.
IR $\nu_{max}^{KBr}$cm$^{-1}$: 1780, 1725, 1645.
$^1$H-NMR δ ppm(DMSO-d$_6$): 4.78–4.06(m, 4H), 3.59(m, 2H), 2.79–1.16(m, 14H), 1.46(d, 3H), 0.87(t, 3H).
Mass(FAB) m/z: 341[(M+H-HCl)$^+$].
[α]$_D$: −78.4° (C=1, methanol).

(Example 20)

Hydrochloride of N-(2-oxo-5-heptyl-3-tetrahydrofuranyl)-L-alanyl-L-proline (Isomer B) [in the formula (I), R$^1$=—(CH$_2$)$_6$CH$_3$, R$^2$=H, R$^3$=CH$_3$, R$^4$ and R$^5$=—(CH$_2$)$_3$—, R$^6$=H (Compound 20)]:
Melting point: 187°–188° C.
IR $\nu_{max}^{KBr}$cm$^{-1}$: 1780, 1705, 1640.
$^1$H-NMR δ ppm(DMSO-d$_6$): 4.77–4.04(m, 4H), 3.58(m, 2H), 2.77–1.10(m, 18H), 1.44(d, 3H), 0.85(t, 3H).
Mass (FAB) m/z: 369[(M+H-HCl)$^+$].
[α]$_D$: −72.2° (C=1, methanol).

(Example 21)

Hydrochloride of N-(2-oxo-5-octyl-3-tetrahydrofuranyl)-L-alanyl-L-proline (Isomer B) [in the formula (I), R$^1$=—(CH$_2$)$_7$CH$_3$, R$^2$=H, R$^3$=CH$_3$, R$^4$ and R$^5$=—(CH$_2$)$_3$—, R$^6$=H (Compound 21)]:
Melting point: 175°–177° C.
IR $\nu_{max}^{KBr}$cm$^{-1}$: 1775, 1705, 1640.
$^1$H-NMR δ ppm(DMSO-d$_6$): 4.76–4.06(m, 4H), 3.58(m, 2H), 2.77–1.10(m, 20H), 1.45(d, 3H), 0.85(t, 3H).
Mass(FAB) m/z: 383[(M+H-HCl)$^+$].
[α]$_D$: −71.3° (C=1, methanol).

Example 22)

Hydrochloride of N-(2-oxo-5-decanyl-3-tetrahydrofuranyl)-L-alanyl-L-proline (Isomer B) [in the formula (I), R$^1$=—(CH$_2$)$_9$CH$_3$, R$^2$=H, R$^3$=CH$_3$, R$^4$ and R$^5$=—(CH$_2$)$_3$—, R$^6$=H (Compound 22)]:
Melting point: 184°–186° C.
IR $\nu_{max}^{KBr}$cm$^{-1}$: 1780, 1705, 1645.
$^1$H-NMR δ ppm(DMSO-d$_6$): 4.74–4.04(m, 4H), 3.58(m, 2H), 2.78–1.10(m, 24H), 1.46(d, 3H), 0.85(t, 3H).
Mass(FAB) m/z: 411[(M+H-HCl)$^+$].
[α]$_D$: −62.1° (C=1, methanol).

(Example 23)

Hydrochloride of N-(2-oxo-5-dodecanyl-3-tetrahydrofuranyl)-L-alanyl-L-proline (Isomer B) [in the formula (I), R$^1$=—(CH$_2$)$_{11}$CH$_3$, R$^2$=H, R$^3$=CH$_3$, R$^4$ and R$^5$=—(CH$_2$)$_3$—, R$^6$=H (Compound 23)]:
Melting point: 177°–179° C.
IR $\nu_{max}^{KBr}$cm$^{-1}$: 1780, 1710, 1645.
$^1$H-NMR δ ppm(DMSO-d$_6$): 4.73–4.04(m, 4H), 3.59(m, 2H), 2.78–1.10(m, 28H), 1.45(d, 3H), 0.85(t, 3H).
Mass(FAB) m/z: 439[(M+H-HCl)$^+$].
[α]$_D$: −48.0° (C=1, methanol).

(Example 24)

Hydrochloride of N-(2-oxo-5-tetradecanyl-3-tetrahydrofuranyl)-L-alanyl-L-proline (Isomer B) [in the formula (I), R$^1$=—(CH$_2$)$_{13}$CH$_3$, R$^2$=H, R$^3$=CH$_3$, R$^4$ and R$^5$=—(CH$_2$)$_3$—, R$^6$=H (Compound 24)]:
Melting point: 178°–180° C.
IR $\nu_{max}^{KBr}$cm$^{-1}$: 1780, 1705, 1645.
$^1$H-NMR δ ppm(DMSO-d$_6$): 4.75–4.04(m, 4H), 3.58(m, 2H), 2.75–1.06(m, 32H), 1.42(d, 3H), 0.84(t, 3H).
Mass(FAB) m/z: 467[(M+H-HCl)$^+$].
[α]$_D$: −46.3° (C=1, methanol).

(Example 25)

Hydrochloride of N-(2-oxo-5-tetrahydrofuranyl)-L-phenylalanyl-L-proline (Isomer B) [in the formula (I), $R^1=R^2=H$, $R^3=CH_2Ph$, $R^4$ and $R^5=-(CH_2)_3-$, $R^6=H$ (Compound 25)]:

Melting point: 143°–145° C.
IR $\nu_{max}^{KBr}$cm$^{-1}$: 1780, 1730, 1645.
$^1$H-NMR δ ppm(DMSO-d$_6$): 7.32(b.s, 5H), 4.86–4.08(m, 5H), 3.72–3.07(m, 4H), 2.93–1.66(m, 6H).
Mass(FAB) m/z: 347[(M+H-HCl)+].
$[α]_D$: −51.3° (C=1, methanol).

(Example 26)

Hydrochloride of N-(2-oxo-3-tetrahydrofuranyl)-L-alanyl-L-proline [in the formula (I), $R^1=R^2=H$, $R^3=CH_3$, $R^4$ and $R^5=-(CH_2)_3-$, $R^6=H$ (Compound 26)]:

Melting point: 125°–129° C.
IR $\nu_{max}^{KBr}$cm$^{-1}$: 1780, 1730, 1645.
$^1$H-NMR δ ppm(DMSO-d$_6$): 4.74–4.04(m, 5H), 3.59(m, 2H), 2.74–1.76(m, 6H), 1.50(d, 1.5H), 1.48(d, 1.5H).
Mass(FAB) m/z: 271[(M+H-HCl)+].
$[α]_D$: −71.5° (C=1, methanol).

Example 27:

Dissolved in 30 ml of acetonitrile was 9.0 g of the pale yellow oily substance obtained in Step (1) of Example 1, followed by an addition of 30 ml of an acetonitrile solution which contained 2.78 g of maleic acid. The resultant mixture was stirred for 30 minutes at room temperature. Crystals which had precipitated were collected by filtration and then recrystalized from acetonitrile, whereby 4.26 g of diastereomers of N-(2-oxo-5-octyl-3-tetrahydrofuranyl)-L-alanine benzyl ester maleate was obtained as colorless crystals. Upon analysis of the diastereomers by high-performance liquid chromatography, a majority of the diasteromers was found to be Isomer B.

Melting point: 143°–144° C.
IR $\nu_{max}^{KBr}$cm$^{-1}$: 1780, 1740.
$^1$H-NMR δ ppm(DMSO-d$_6$): 7.33(s, 5H), 6.17(s, 2H), 5.13(s, 2H), 4.59–4.16(m, 1H), 3.92–3.51(m, 2H), 2.59–1.98(m, 1H), 1.80–1.10(m, 18H), 0.86(t, 3H).
Mass(FAB) m/z: 376[(M+H-HOOCCHCH-COOH)+].
$[α]_D$: +3.2° (C=1, methanol).

Example 28

Dissolved in 8 ml of acetonitrile was 1.40 g of the white powder of Compound 14 obtained in Example 14, followed by an addition of 8 ml of an acetonitrile solution which contained 0.45 g of maleic acid. The resultant mixture was stirred for 1 hour at room temperature. Crystals which had precipitated were collected by filtration and then recrystalized from acetonitrile, whereby 1.35 g of the maleate of Compound 14 was obtained as colorless crystals.

Melting point: 121°–122° C.
IR $\nu_{max}^{KBr}$cm$^{-1}$: 1775, 1705, 1640.
$^1$H-NMR δ ppm(DMSO-d$_6$): 6.12(s, 2H), 4.50–3.72(m, 4H), 3.54(m, 2H), 2.66–1.12(m, 16H), 1.22(d, 3H), 0.85(t, 3H).
Mass(FAB) m/z: 355[(M+H-HOOCCHCH-COOH)+].
$[α]_D$: −58.1° (C=1, methanol).

Examples 29–32

Conducting a reaction and treatments in the same manner as in Example 28 except for the separate use of the white powders of Compounds 16 and 19–21 instead of the white powder of Compound 14, the maleates of Compounds 16 and 19–21 given below in Examples 29–32 were each obtained as colorless crystals.

(Example 29)

Maleate of Compound 16:
Melting point: 143°–144° C.
IR $\nu_{max}^{KBr}$cm$^{-1}$: 1775, 1730, 1645.
$^1$H-NMR δ ppm(DMSO-d$_6$): 6.12(s, 2H), 4.50–3.74(m, 4H), 3.54(m, 2H), 2.70–1.50(m, 8H), 1.28(d, 3H), 0.93(t, 3H).
Mass(FAB) m/z: 299[(M+H-HOOCCHCH-COOH)+].
$[α]_D$: −64.4° (C=1, methanol).

(Example 30)

Maleate of Compound 19:
Melting point: 135°–135° C.
IR $\nu_{max}^{KBr}$cm$^{-1}$: 1780, 1735, 1650.
$^1$H-NMR δ ppm(DMSO-d$_6$): 6.12(s, 2H), 4.50–3.70(m, 4H), 3.54(m, 2H), 2.70–1.12(m, 14H), 1.27(d, 3H), 0.88(t, 3H).
Mass(FAB) m/z: 341[(M+H-HOOCCHCH-COOH)+].
$[α]_D$: −56.2° (C=1, methanol).

(Example 31)

Maleate of Compound 20:
Melting point: 117°–118° C.
IR $\nu_{max}^{KBr}$cm$^{-1}$: 1775, 1705, 1645.
$^1$H-NMR δ ppm(DMSO-d$_6$): 6.11(s, 2H), 4.48–3.70(m, 4H), 3.53(m, 2H), 2.68–1.12(m, 21H), 0.86(t, 3H).
Mass(FAB) m/z: 369[(M+H-HOOCCHCH-COOH)+].
$[α]_D$: −52.4° (C=1, methanol).

(Example 32)

Maleate of Compound 21:
Melting point: 123°–124° C.
IR $\nu_{max}^{KBr}$cm$^{-1}$: 1775, 1705, 1645.
$^1$H-NMR δ ppm(DMSO-d$_6$): 6.12(s, 2H), 4.50–3.70(m, 4H), 3.53(m, 2H), 2.68–1.12(m, 23H), 0.86(t, 3H).
Mass(FAB) m/z: 383[(M+H-HOOCCHCH-COOH)+].
$[α]_D$: −47.0° (C=1, methanol).

Example 33

Dissolved in 50 ml of acetonitrile were 2.00 g of N$^ε$-t-butoxycarbonyl-L-lysyl-L-proline t-butyl ester and 3.53 g of 2-bromo-4-pentyl-γ-butyrolactone. After a dropwise addition of 0.76 g of triethylamine, the resultant mixture was heated and stirred at 70° C. for 40 hours. The reaction mixture was poured into chilled water, followed by extraction with ethyl acetate. The extract was washed successively with water, a 2% aqueous solution of sodium hydrogencarbonate, and water. After drying the extract over anhydrous sodium sulfate, it was distilled under reduced pressure. The residue was isolated and purified by chromatography on a silica gel column (chloroform:ethyl acetate=10-:1–5:1), thereby obtaining as a colorless syrupy substance 2.00 g of N$^\alpha$-(2-oxo-5-pentyl-3-tetrahydrofuranyl)-N$^\epsilon$-t-butoxycarbonyl-L-lysyl-L-proline t-butyl ester [in the formula (I), R$^1$=—(CH$_2$)$_4$CH$_3$, R$^2$=H, R$^3$=—(CH$_2$)$_4$NHCOO-t-Bu, R$^4$ and R$^5$=—(CH$_2$)$_3$—, R$^6$=t-Bu (Compound 27)]. Upon analysis of Compound 27 by high-performance liquid chromatography, it was found to be a mixture of 4 types of diastereomers.

IR $\nu_{max}^{neat}$cm$^{-1}$: 1775, 1735, 1710, 1640.

$^1$H-NMR δ ppm(CDCl$_3$): 4.88–4.05 (m, 3H), 3.76–3.26 (m, 3H), 3.10 (m, 2H), 2.64–1.16 (m, 20H), 1.45 (s, 9H), 1.43 (s, 9H), 0.86 (t, 3H).

Mass (EI) m/z: 553 (M+).

[α]$_D$: −50.5° (C=1, methanol).

Example 34

Conducting a reaction and treatments in the same manner as in Example 33 except for the use of 2-bromo-4-heptyl-γ-butyrolactone instead of 2-bromo-4-pentyl-γ-butyrolactone, was obtained as a colorless syrupy substance N$^\alpha$-(2-oxo-5-heptyl-3-tetrahydrofuranyl)-N$^\epsilon$-t-butoxycarbonyl-L-lysyl-L-proline t-butyl ester [In the formula (I), R$^1$=—(CH$_2$)$_6$CH$_3$, R$^2$=H, R$^3$=—(CH$_2$)$_4$NHCOO—t—Bu, R$^4$ and R$^5$=—(CH$_2$)$_3$—, R$^6$=t-Bu Compound 28)].

IR $\nu_{max}^{neat}$cm$^{-1}$: 1775, 1735, 1710, 1645.

$^1$H-NMR δ ppm(CDCl$_3$): 4.90–4.07 (m, 3H), 3.76–3.28 (m, 3H), 3.10 (m, 2H), 2.64–1.10 (m, 24H), 1.45 (s, 9H), 1.43 (s, 9H), 0.86 (t, 3H).

Mass (EI) m/z: 581 (M+).

[α]$_D$: −52.0° (C=1, methanol).

Example 35

Dissolved in 100 ml of acetonitrile were 4.00 g of N$^\epsilon$-t-butoxycarbonyl-L-lysyl-L-proline t-butyl ester and 5.00 g of 2-bromo-4-hexyl-γ-butyrolactone. After an addition of 1.52 g of triethylamine, the resultant mixture was heated and stirred at 80° C. for 24 hours. The reaction mixture was concentrated under reduced pressure, followed by separation in an ethyl acetate-water system. The organic layer was washed successively with a 2% aqueous solution of sodium hydrogencarbonate and water. After drying the ethyl acetate solution over anhydrous sodium sulfate, it was distilled under reduced pressure. The residue was isolated and purified by chromatography on a silica gel column (chloroform:methanol=500:1–50:1). From initial fractions of the column effluent, 2.39 g of a colorless syrupy substance was obtained. The syrupy substance was dissolved in 3 ml of acetonitrile, followed by an addition of 8 ml of an acetonitrile solution which contained 0.46 g of maleic acid. The thus-obtained mixture was stirred for 30 minutes at room temperature and was thereafter allowed to stand overnight at 4° C. Crystals which had precipitated were collected by filtration. After washing the crystals with a small amount of chilled acetonitrile, they were dried to obtain as colorless crystals 1.52 g of the maleate of N$^\alpha$-(2-oxo-5-hexyl-3-tetrahydrofuranyl)-N$^\epsilon$-t-butoxycarbonyl-L-lysyl-L-proline t-butyl ester (Isomer B) [in the formula (I), R$^1$=—(CH$_2$)$_5$CH$_3$, R$^2$=H, R$^3$=—(CH$_2$)$_4$NHCOO—t—Bu, R$^4$ and R$^5$=—(CH$_2$)$_3$—, R$^6$=t—Bu (Compound 29)].

Melting point: 144°–145° C.

IR $\nu_{max}^{KBr}$cm$^{-1}$: 1775, 1725, 1700, 1655.

$^1$H-NMR δ ppm(DMSO-d$_6$): 6.16 (s, 2H), 4.52–3.32 (m, 6H), 2.91 (m, 2H), 2.66–1.10 (m, 22H), 1.38 (s, 9H), 1.36 (s, 9H), 0.87 (t, 3H).

Mass (FAB) m/z: 568 [(M+H—HOOCCHCH-COOH)+].

[α]$_D$: −52.5° (C=1, methanol).

From still subsequent fractions of the column effluent, 2.23 g of a colorless syrupy substance was obtained. The syrupy substance was dissolved in 3 ml of acetonitrile, followed by an addition of 8 ml of an acetonitrile solution which contained 0.44 g of maleic acid. The thus-obtained mixture was stirred for 30 minutes at room temperature and was thereafter allowed to stand overnight at 4° C. Crystals which had precipitated were collected by filtration. Upon recrystallization of the crystals from ethyl acetate, was obtained as colorless crystals 1.28 g of N$^\alpha$-(2-oxo-5-hexyl-3-tetrahydrofuranyl)-N$^\epsilon$-t-butoxycarbonyl-L-lysyl-L-proline t-butyl ester (Isomer A) [in the formula (I), R$^1$=—(CH$_2$)$_5$CH$_3$, R$^2$=H, R$^3$=—(CH$_2$)$_4$NHCOO—t—Bu, R$^4$ and R$^5$=—(CH$_2$)$_3$—, R$^6$=t—Bu (Compound 30)].

Melting point: 132°–133° C.

IR $\nu_{max}^{KBr}$cm$^{-1}$: 1780, 1720, 1700, 1650.

$^1$H-NMR δ ppm(DMSO-d$_6$): 6.18 (s, 2H), 4.48–3.32 (m, 6H), 2.92 (m, 2H), 2.66–1.10 (m, 22H), 1.38 (s, 9H), 1.36 (s, 9H), 0.87 (t, 3H).

Mass (FAB) m/z: 568 [(M+H—HOOCCHCH-COOH)+].

[α]$_D$: −44.3° (C=1, methanol).

These Isomers A and B were analyzed separately by high-performance liquid chromatography. They were each found to be a single diastereomer.

Examples 36–38

Compounds given below in Examples 36–38 were separately obtained by providing their corresponding 2-halo-4-alkyl-γ-butyrolactone and then conducting their reactions and treatments in the same manner as in Example 35.

(Example 36)

Maleate of N$^\alpha$-(2-oxo-5-butyl-3-tetrahydrofuranyl)-N$^\epsilon$-t-butoxycarbonyl-L-lysyl-L-proline t-butyl ester (Isomer B) [in the formula (I), R$^1$=—(CH$_2$)$_3$CH$_3$, R$^2$=H, R$^3$=—(CH$_2$)$_4$NHCOO—t-Bu, R$^4$ and R$^5$=—(CH$_2$)$_3$—, R$^6$=t—Bu (Compound 31)]:

Melting point: 147°–148° C.

IR $\nu_{max}^{KBr}$cm$^{-1}$: 1780, 1715, 1695, 1650.

$^1$H-NMR δ ppm(DMSO-d$_6$): 6.18 (s, 2H), 4.52–3.32 (m, 6H), 2.93 (m, 2H), 2.67–1.10 (m, 18H), 1.40 (s, 9H), 1.38 (s, 9H), 0.90 (t, 3H).

Mass (FAB) m/z: 540 [(M+H—HOOCCHCH-COOH)+].

[α]$_D$: −50.7° (C=1, methanol).

(Example 37)

Maleate of N$^\alpha$-(2-oxo-5-pentyl-3-tetrahydrofuranyl)-N$^\epsilon$-t-butoxycarbonyl-L-lysyl-L-proline t-butyl ester (Isomer B) [in the formula (I), R$^1$=—(CH$_2$)$_4$CH$_3$, R$^2$=H, R$^3$=—(CH$_2$)$_4$NHCOO—t—Bu, R$^4$ and R$^5$=—(CH$_2$)$_3$—, R$^6$=t—Bu (Compound 32)]:

Melting point: 139°–140° C.

IR $\nu_{max}^{KBr}$cm$^{-1}$: 1780, 1715, 1700, 1650.

$^1$H-NMR δ ppm(DMSO-d$_6$): 6.17 (s, 2H), 4.48–3.86 (m, 3H), 3.82–3.32 (m, 3H), 2.92 (m, 2H), 2.66–1.10 (m, 20H), 1.39 (s, 9H), 1.37 (s, 9H), 0.88 (t, 3H).

Mass (FAB) m/z: 554 [(M+H—HOOCCHCH-COOH)+].

[α]$_D$: −50.9° (C=1, methanol).

(Example 38)

Maleate of N$^\alpha$-(2-oxo-5-cyclohexyl-3-tetrahydrofuranyl)-N$^\epsilon$-t-butoxycarbonyl-L-lysyl-L-proline t-butyl ester (Isomer B) [in the formula (I),

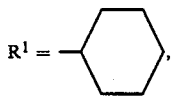

R$^2$=H, R$^3$=—(CH$_2$)$_4$NHCOO—t—Bu, R$^4$ and R$^5$=—(CH$_2$)$_3$—, R$^6$=t—Bu (Compound 33)]:
Melting point: 162°–163° C.
IR $\nu_{max}^{KBr}$cm$^{-1}$: 1775, 1715, 1700, 1650.
$^1$H-NMR δ ppm(DMSO-d$_6$): 6.13 (s, 3H), 4.38–3.88 (m, 3H), 3.82–3.30 (m, 3H), 2.90 (m, 2H), 2.64–0.94 (m, 23H), 1.37 (s, 18H).
Mass (FAB) m/z: 566[(M+H-HOOCCHCHCOOH)+].
[α]$_D$: −48.9° (C=1, methanol).

EXAMPLE 39

The colorless syrupy substance (4.20 g) obtained in Example 34 was dissolved in 3 ml of acetonitrile, followed by an addition of 12 ml of an acetonitrile solution which contained 0.80 g of maleic acid. The thus-obtained mixture was stirred for 30 minutes at room temperature and was thereafter allowed to stand overnight at 4° C. Crystals which had precipitated were collected by filtration. After washing the crystals with a small amount of chilled acetonitrile, they were dried to obtain as colorless crystals 0.92 g of the maleate of N$^\alpha$-(2-oxo-5-heptyl-3-tetrahydrofuranyl)-N$^\epsilon$-t-butoxycarbonyl-L-lysyl-L-proline t-butyl ester (Isomer B) [in the formula (I), R$^1$=—(CH$_2$)$_6$CH$_3$, R$^2$=H, R$^3$=—(CH$_2$)$_4$NHCOO-t-Bu, R$^4$ and R$^5$=—(CH$_2$)$_3$—, R$^6$=t-Bu (Compound 34)].
Melting point: 121°–122° C.
IR $\nu_{max}^{KBr}$cm$^{-1}$: 1775, 1735, 1695, 1655.
$^1$H-NMR δ ppm(DMSO-d$_6$): 6.15 (s, 2H), 4.50–3.86 (m, 3H), 3.80–3.32 (m, 3H), 2.91 (m, 2H), 2.64–1.10 (m, 24 H), 1.39 (s, 9H), 1.37 (s, 9H), 0.86 (t, 3H).
Mass (FAB) m/z: 582 [(M+H—HOOCCHCHCOOH)+].
[α]$_D$: −46.2° (C=1, methanol).

(Example 40)

To 1.13 g of the maleate of N$^\alpha$-(2-oxo-5-hexyl-3-tetrahydrofuranyl)-N$^\epsilon$-t-butoxycarbonyl-L-lysyl-L-proline (t-butyl ester) (Isomer B) (Compound 29), 50 ml of ethyl acetate and 20 ml of a saturated aqueous solution of sodium hydrogencarbonate. The resulting mixture was stirred for 30 minutes at room temperature. The water layer was removed. The organic layer was washed with a saturated saline, dried over anhydrous sodium sulfate, and then distilled under reduced pressure. The residue was dissolved in 20 ml of a 4N HCl-dioxane solution, followed by stirring at room temperature for 5 hours. The reaction mixture was concentrated under reduced pressure. Ethyl acetate was added to the concentrate and the resulting crystals were collected by filtration. Those crystals were washed with ethyl acetate and then with ether and were thereafter dried to obtain as colorless crystals 0.80 g of the dihydrochloride of N$^\alpha$-(2-oxo-5-hexyl-3-tetrahydrofuranyl)-L-lysyl-L-proline (Isomer B) [in the formula (I), R$^1$=—(CH$_2$)$_5$CH$_3$, R$^2$=H, R$^3$=—(CH$_2$)$_4$NH$_2$, R$^4$ and R$^5$=—(CH$_2$)$_3$—, R$^6$=H (Compound 35)].
Melting point: 153°–155° C.
IR $\nu_{max}^{KBr}$cm$^{-1}$: 1775, 1720, 1645.
$^1$H-NMR δ ppm(DMSO-d$_6$): 8.04 (br, 2H), 4.70–4.08 (m, 4H), 3.60 (m, 2H), 2.90–2.52 (m, 3H), 2.32–1.10 (m, 21H), 0.86 (t, 3H).
Mass (FAB) m/z: 412 [(M+H—2HCL)+].
[α]$_D$: −47.6° (C=1, methanol).

Examples 41–45

Conducting a reaction and treatments in the same manner as in Example 40 except for the separate use of the maleates of Compounds 30–34 instead of the maleate of Compound 29, the dichlorides of Compounds 36–40 given below in Examples 41–45 were each obtained as colorless crystals.

(Example 41)

Dihydrochloride of N$^\alpha$-(2-oxo-5-hexyl-3-tetrahydrofuranyl)-L-lysyl-L-proline (Isomer A) [in the formula (I), R$^1$=—(CH$_2$)$_5$CH$_3$, R$^2$=H, R$^3$=—(CH$_2$)$_4$NH$_2$, R$^4$ and R$_5$=—(CH$_2$)$_3$—, R$^6$=H (Compound 36)]:
Melting point: 143°–145° C.
IR $\nu_{max}^{KBr}$cm$^{-1}$: 1775, 1720, 1640.
$^1$H-NMR δ ppm(DMSO-d$_6$): 8.06 (br, 2H), 4.60–4.10 (m, 4H), 3.62 (m, 2H), 2.88–2.54 (m, 3H), 2.32–1.10 (m, 21H), 0.86 (t, 3H).
Mass (FAB) m/z: 412 [(M+H—2HCl)+].
[α]$_D$: −30.7° (C=1, methanol).

(Example 42)

Dihydrochloride of N$^\alpha$-(2-oxo-5-butyl-3-tetrahydrofuranyl)-L-lysyl-L-proline (Isomer B) [in the formula (I), R$^1$=—(CH$_2$)$_3$CH$_3$, R$^2$=H, R$^3$=—(CH$_2$)$_4$NH$_2$, R$^4$ and R$^5$=—(CH$_2$)$_3$—, R$^6$=H (Compound 37)]:
Melting point: 150°–152° C.
IR $\nu_{max}^{KBr}$cm$^{-1}$: 1770, 1725, 1640.
$^1$H-NMR δ ppm(DMSO-d$_6$): 8.10 (br, 2H), 4.60–4.12 (m, 4H), 3.60 (m, 2H), 2.90–2.56 (m, 3H), 2.36–1.12 (m, 17H), 0.90 (t, 3H).
Mass (FAB) m/z: 384 [(M+H—2HCl)+].
[α]$_D$: −45.9° (C=1, methanol).

(Example 43)

Dihydrochloride of N$^\alpha$-(2-oxo-5-pentyl-3-tetrahydrofuranyl)-L-lysyl-L-proline (Isomer B) [in the formula (I), R$^1$=—(CH$_2$)$_4$CH$_3$, R$^2$=H, R$^3$=—(CH$_2$)$_4$NH$_2$, R$^4$ and R$^5$=—(CH$_2$)$_3$—, R$^6$=H (Compound 38)]:
Melting point: 158°–160° C.
IR $\nu_{max}^{KBr}$cm$^{-1}$: 1775, 1720, 1640.
$^1$H-NMR δ ppm(DMSO-d$_6$): 8.06 (br, 2H), 4.66–4.10 (m, 4H), 3.60 (m, 2H), 2.86–2.56 (m, 3H), 2.34–1.10 (m, 19H), 0.87 (t, 3H).
Mass (FAB) m/z: 398 [(M+H—2HCl)+].
[α]$_D$: −38.4° (C=1, methanol).

(Example 44)

Dihydrochloride of N$^\alpha$-(2-oxo-5-cyclohexyl-3-tetrahydrofuranyl)-L-lysyl-L-proline (Isomer B) [in the formula (I),

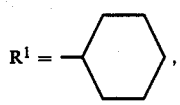

$R^2=H$, $R^3=-(CH_2)_4NH_2$, $R^4$ and $R^5=-(CH_2)_3-$, $R^6=H$ (Compound 39)]:

Melting point: 179°–181° C.

IR $\nu_{max}^{KBr}$cm$^{-1}$: 1770, 1720, 1645.

$^1$H-NMR δ ppm(DMSO-d$_6$): 8.04 (br, 2H), 4.78–4.08 (m, 4H), 3.62 (m, 2H), 2.88–2.56 (m, 3H), 2.32–0.86 (m, 22H).

Mass (FAB) m/z: 410 [(M+H—2HCl)+].

[α]$_D$: −44.5° (C=1, methanol).

(Example 45)

Dihydrochloride of N$^α$-(2-oxo-5-heptyl-3-tetrahydrofuranyl)-L-lysyl-L-proline (Isomer B) [in the formula (I), $R^1=-(CH_2)_6CH_3$, $R^2=H$, $R^3=-(CH_2)_4NH_2$, $R^4$ and $R^5=-(CH_2)_3-$, $R^6=H$ (Compound 40)]:

Melting point: 157°–159° C.

IR $\nu_{max}^{KBr}$cm$^{-1}$: 1775, 1730, 1645.

$^1$H-NMR δ ppm(DMSO-d$_6$): 8.06 (br, 2H), 4.72–4.07 (m, 4H), 3.62 (m, 2H), 2.92–2.52 (m, 3H), 2.30–1.06 (m, 23H), 0.86 (t, 3H).

Mass (FAB) m/z: 426 [(M+H—2HCl)+].

[α]$_D$: −42.8° (C=1, methanol).

Example 46

A 4N HCl-dioxane solution was added to the colorless syrupy substance of Compound 27 obtained in Example 33. Thereafter, a reaction and treatments were conducted in the same manner as in Example 40 to obtain as colorless crystals the dihydrochloride of N$^α$-(2-oxo-5-pentyl-3-tetrahydrofuranyl)-L-lysyl-L-proline [in the formula (I), $R^1=-(CH_2)_4CH_3$, $R^2=H$, $R^3=-(CH_2)_4NH_2$, $R^4$ and $R^5=-(CH_2)_3-$, $R^6=H$ (Compound 41)].

Melting point: 141°–143° C.

IR $\nu_{max}^{KBr}$cm$^{-1}$: 1775, 1730, 1645.

$^1$H-NMR δ ppm(DMSO-d$_6$): 8.10 (br, 2H), 4.78–4.06 (m, 4H), 3.64 (m, 2H), 2.94–2.52 (m, 3H), 2.32–1.10 (m, 19H), 0.87 (t, 3H).

Mass (FAB) m/z: 398 [(M+H—2HCl)+].

[α]$_D$: −44.6° (C=1, methanol).

Example 47

A reaction was carried out in the same manner as in Example 33 except that L-alanyl-N-cyclopentylglycine t-butyl ester was used in lieu of N$^ε$-t-butoxycarbonyl-L-lysyl-L-proline t-butyl ester. The residue was isolated and purified by chromatography on a silica gel column (chloroform:ethyl acetate=100:1–20:1). From initial fractions of the column effluent, was obtained as a colorless syrupy substance N-(2-oxo-5-pentyl-3-tetrahydrofuranyl)-L-alanyl-N-cyclopentylglycine t-butyl ester (Isomer B) [In the formula (I), $R^1=-(CH_2)_4CH_3$, $R^2=H$, $R^3=CH_3$,

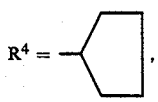

$R^5=H$, $R^6=t-Bu$ (Compound 42)].

IR $\nu_{max}^{neat}$cm$^{-1}$: 1780, 1735, 1640.

$^1$H-NMR δ ppm(CDCl$_3$): 4.57–4.10 (m, 3H), 3.82 (b.s, 2H), 3.42 (m, 1H), 2.51 (m, 1H), 2.16–1.10 (m, 17H), 1.44 (s, 9H), 0.86 (t, 3H).

From subsequent fractions of the column effluent, a mixture of the other three types of diastereomers was obtained as a colorless syrupy substance.

Example 48

Conducting a reaction and treatments in the same manner as in Example 47 except for the use of 2-bromo-4-octyl-γ-butyrolactone in place of 2-bromo-4-pentyl-γ-butyrolactone, was obtained as a colorless syrupy substance t-butyl N-(2-oxo-5-octyl-3-tetrahydrofuranyl)-L-alanyl-N-cyclopentylglycine t-butyl ester (Isomer B) [In the formula (I), $R^1=-(CH_2)_7CH_3$, $R^2=H$, $R^3=CH_3$,

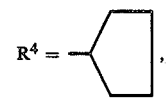

$R^5=H$, $R^6=t-Bu$ (Compound 43)].

IR $\nu_{max}^{neat}$cm$^{-1}$: 1780, 1735, 1645.

$^1$H-NMR δ ppm(CDCl$_3$): 4.56–4.10 (m, 3H), 3.81 (b.s, 2H), 3.40 (m, 1H), 2.50 (m, 1H), 2.17–1.08 (m, 23H), 1.44 (s, 9H), 0.85 (t, 3H).

Examples 49 and 50

Compounds 42 and 43 obtained in Examples 47 and 48 were separately added with a 4N HCl-dioxane solution. A reaction and treatments were then conducted in the same manner as in Example 40, whereby the hydrochlorides of Compounds 44 and 45 given below in Examples 49 and 50 were each obtained as colorless crystals.

Example 49

Hydrochloride of N-(2-oxo-5-pentyl-3-tetrahydrofuranyl)-L-alanyl-N-cyclopentylglycine (Isomer B) [in the formula (I), $R^1=-(CH_2)_4CH_3$, $R^2=H$, $R^3=CH_3$,

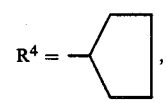

$R^5=H$, $R^6=H$ (Compound 44)]:

Melting point: 213°–216° C.

IR $\nu_{max}^{KBr}$cm$^{-1}$: 1780, 1730, 1650.

$^1$H-NMR δ ppm(DMSO-d$_6$): 4.98–3.96 (m, 4H), 3.88 (b.s, 2H), 2.80–1.04 (m, 18H), 0.88 (t, 3H).

Mass (FAB) m/z: 369 [(M+H—HCl)+].

[α]$_D$: −14° (C=0.1, methanol).

Example 50 Hydrochloride of

N-(2-oxo-5-octyl-3-tetrahydrofuranyl)-L-alanyl-N-cyclopentylglycine (Isomer B) [in the formula (I), $R^1=-(CH_2)_7CH_3$, $R^2=H$, $R^3=CH_3$,

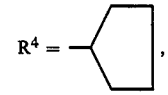

$R^5$=H, $R^6$=H (Compound 45)]:
 Melting point: 177°–179° C.
 IR $\nu_{max}^{KBr}$cm$^{-1}$: 1775, 1730, 1650.
 $^1$H-NMR δ ppm(DMSO)-d$_6$): 4.95–4.00(m, 4H), 3.90(b.s, 2H), 2.82–1.00(m, 24H), 0.86(t, 3H).
 Mass(FAB) m/z: 411[(M+H—HCl)$^+$].
 [α]$_D$: −19° (C=0.1, methanol).

Example 51

(1) A pale yellow oily substance was obtained by conducting a reaction in the same manner as in Step (1) of Example 1 except for the use of 1-oxa-2-oxo-3-bromospiro[4.5]decane in lieu of 2-bromo-4-octyl-γ-butyrolactone. N-(1-oxa-2-oxospiro[4.5]decan-3-yl)-(S)-alanine benzyl ester was contained in the oily substance. As a result of an analysis of the benzyl ester by high-performance liquid chromatography, it was found to be a mixture of two types of diastereomers.

The pale yellow oily substance was then isolated and purified by chromatography on a silica gel column (toluene:ethyl acetate=25:1–2:1). From initial fractions of the column effluent, N-[1-oxa-2-oxospiro[4.5]decan-3(R)-yl]-(S)-alanine benzyl ester was obtained as colorless crystals.
 Melting Point: 48°–50° C.
 IR $\nu_{max}^{neat}$cm$^{-1}$: 3320, 1775, 1735.
 $^1$H-NMR δ ppm(CDCl$_3$): 7.34(s, 5H), 5.16(s, 2H), 3.61(d.d, 1H), 3.42(d.d, 1H), 2.32(m, 1H), 1.88–1.28(m, 11H), 1.33(d, 3H).
 Mass(EI) m/z: 331(M$^+$).
 [α]$_D$: −16.3° (C=0.5, methanol).

From subsequent fractions of the column effluent, N-[1-oxa-2-oxospiro[4.5]decan-3(S)-yl]-(S)-alanine benzyl ester was obtained as a colorless oily substance.
 IR $\nu_{max}^{neat}$cm$^{-1}$: 3330, 1770, 1735.
 $^1$H-NMR δ ppm(CDCl$_3$): 7.34(s, 5H), 5.14(s, 2H), 3.81(d.d, 1H), 3.61(d.d, 1H), 2.32(m, 1H), 1.92–1.28(m, 11H), 1.34(d, 3H).
 Mass(EI) m/z: 331(M$^+$).
 [α]$_D$: −21.8° (C=0.5, methanol).

(2) A reaction and treatments were conducted in the same manner as in Step (2) of Example 1 by using N-[1-oxa-2-oxospiro[4.5]decan-3(S)-yl]-(S)-alanine benzyl ester, thereby obtaining N-[1-oxa-2-oxospiro-[4.5]decan-3(S)-yl]-(S)-alanine as colorless crystals.
 Melting Point: 185°–187° C.
 IR $\nu_{max}^{KBr}$cm$^{-1}$: 3420, 1785.
 $^1$H-NMR δ ppm(DMSO-d$_6$): 3.71(d.d, 1H), 3.55(d.d, 1H), 2.37(m, 1H), 1.76–1.28(m, 11H), 1.19(d, 3H).
 Mass(FAB) m/z: 242[(M+H)$^+$].

(3) A reaction was conducted in the same manner as in Step (3) of Example 1 except that N-[1-oxa-2-oxospiro[4.5]decan-3(S)-yl]-(S)-alanine was used instead of Isomer BCD of N-[2-oxo-5-octyl-3-tetrahydrofuranyl]-L-alanine. The residue was purified by chromatography on a silica gel column (chloroform:ethyl acetate=3:1), thereby obtaining as a colorless syrupy substance N-[1-oxa-2-oxospiro[4.5]decan-3(S)-yl]-(S)-alanyl-(S)-proline benzyl ester [in the formula (I), R$^1$ and R$^2$=—(CH$_2$)$_5$—, R$^3$=CH$_3$, R$^4$ and R$^5$=—(CH$_2$)$_3$—, R$^6$=—CH$_2$Ph (Compound 46)].
 IR $\nu_{max}^{neat}$cm$^{-1}$: 3320, 1770, 1740, 1640.
 $^1$H-NMR δ ppm(CDCl$_3$): 7.32(s, 5H), 5.20(d, 1H), 5.03(d, 1H), 4.54(m, 1H), 3.90–3.32(m, 4H), 2.42–1.10(m, 16H), 1.20(d, 1H).
 Mass(EI) m/z: 428(M$^+$).
 [α]$_D$: −70.8° (C=0.5, methanol).

Example 52

A reaction was conducted in the same manner as in Example 35 except for the use of 1-oxa-2-oxo-3-bromospiro[4.5]decane instead of 2-bromo-4-hexyl-γ-butyrolactone. The residue was isolated and purified by chromatography on a silica gel column (chloroform:methanol=200:1–20:1). Obtained as a colorless syrupy substance from initial fractions of the column effluent was N$^α$-[1-oxa-2-oxospiro[4.5]decan-3(S)-yl]-N$^ε$-t-butoxycarbonyl-(S)-lysyl-(S)-proline t-butyl ester [in the formula (I), R$^1$ and R$^2$=—(CH$_2$)$_5$—, R$^3$=—(CH$_2$)$_4$NHCOO-t-Bu, R$^4$ and R$^5$=—(CH$_2$)$_3$—, R$^6$=t-Bu (Compound 47)].
 IR $\nu_{max}^{neat}$cm$^{-1}$: 1770, 1735, 1700, 1640.
 $^1$H-NMR δ ppm(CDCl$_3$): 4.90–4.24(m, 2H), 3.84–3.36(m, 3H), 3.10(m, 2H), 2.46–1.20(m, 22H), 1.44(s, 9H) 1.42(s, 9H).
 Mass(EI) m/z: 551(M$^+$).

From subsequent fractions of the column effluent, was obtained as a colorless syrupy substance N$^α$-[1-oxa-2-oxospiro[4.5]decan-3(R)-yl]-N$^ε$-t-butoxycarbonyl-(S)-lysyl-(S)-proline t-butyl ester [in the formula (I), R$^1$ and R$^2$=—(CH$_2$)$_5$—, R$^3$=—(CH$_2$)$_4$NHCOO-t-Bu, R$^4$ and R$^5$=—(CH$_2$)$_3$—, R$^6$=t-Bu (Compound 48)].
 IR $\nu_{max}^{neat}$cm$^{-1}$: 1770, 1730, 1700, 1640.
 $^1$H-NMR δ ppm(CDCl$_3$): 4.90–4.32(m, 2H), 3.82–3.30(m, 3H), 3.10(m, 2H), 2.48–1.20(m, 22H), 1.43(s, 9H), 1.41(s, 9H).
 Mass(EI) m/z: 551(M$^+$).

Example 53

A reaction similar to that conducted in Example 14 and treatments similar to those carried out in Example 28 were effected using Compound 46 instead of Compound 7 in Example 14, thereby obtaining as colorless crystals the maleate of N-[1-oxa-2-oxospiro-[4.5]decan-3(S)-yl]-(S)-alanyl-(S)-proline [in the formula (I), R$^1$ and R$^2$=—(CH$_2$)$_5$—, R$^3$=CH$_3$, R$^4$ and R$^5$=—(CH$_2$)$_3$—, R$^6$=H (Compound 49)].
 Melting Point: 118°–120° C.
 IR $\nu_{max}^{KBr}$cm$^{-1}$: 1775, 1705, 1645.
 $^1$H-NMR δ ppm(CD$_3$COCD$_3$): 6.30(s, 2H), 4.56–3.84(m, 3H), 3.70(m, 2H), 2.78–1.20(m, 19H).
 Mass(FAB) m/z: 339[(M+H—HOOCCHCHCOOH)$^+$].
 [α]$_D$: −38.5° (C=0.5, methanol).

Example 54

A 4N HCl-dioxane solution was added to the colorless syrupy substance of Compound 47 obtained in Example 52. Thereafter, a reaction and treatments were conducted in the same manner as in Example 40 to obtain as colorless crystals the dihydrochloride of N$^α$-[1-oxa-2-oxospiro[4.5]decan-3(S)-yl]-(S)-lysyl-(S)-proline [in the formula (I), R$^1$ and R$^2$=—(CH$_2$)$_5$—, R$^3$=—(CH$_2$)$_4$NH$_2$, R$^4$ and R$^5$=—(CH$_2$)$_3$—, R$^6$=H (Compound 50)].
 Melting Point: 178°–180° C.
 IR $\nu_{max}^{KBr}$cm$^{-1}$: 1770, 1720, 1640.
 $^1$H-NMR δ ppm(DMSO-d$_6$): 8.00(br, 2H), 4.86–4.08(m, 3H), 3.60(m, 2H), 2.85–2.56(m, 3H), 2.30–1.20(m, 21H).
 Mass(FAB) m/z: 396[(M+H—2HCl)$^+$].
 [α]$_D$: −52.2° (C=0.5, methanol).

Examples 55-57

Compounds given below in Examples 55-57 were separately obtained as colorless syrupy substances by using their corresponding 2-halo-4,4-dialkyl-γ-butyrolactone or 1oxa-2-oxo-3-bromospiro[4.6]undecane and conducting a reaction similar to that conducted in Example 35 and treatments similar to those carried out in Example 52.

Example 55

$N^\alpha$-[2-oxo-5,5-dipentyl-3(S)-tetrahydrofuranyl]-$N^\epsilon$-t-butoxycarbonyl-(S)-lysyl-(S)-proline t-butyl ester [in the formula (I), $R^1=-(CH_2)_4CH_3$, $R^2=-(CH_2)_4CH_3$, $R^3=(CH_2)_4NHCOO$-t-Bu, $R^4$ and $R^5=-(CH_2)_3-$, $R^6=$t-Bu (Compound 51)]:

IR $\nu_{max}^{neat}$cm$^{-1}$: 1770, 1735, 1700, 1640.

$^1$H-NMR δ ppm(CDCl$_3$): 4.92–4.26(m, 2H), 3.82–3.40(m, 3H), 3.09(m, 2H), 2.44–1.08(m, 28H), 1.43(s, 9H), 1.41(s, 9H), 0.87(t, 6H).

Mass(EI) m/z: 623(M+).

[α]$_D$: −63.1° (C=0.5, methanol).

Example 56

$N^\alpha$-[2-oxo-5,5-dihexyl-3(S)-tetrahydrofuranyl]-$N^\epsilon$-t-butoxycarbonyl-(S)-lysyl-(S)-proline t-butyl ester [in the formula (I), $R^1=-(CH_2)_5CH_3$, $R^2=-(CH_2)_5CH_3$, $R^3=(CH_2)_4NHCOO$-t-Bu, $R^4$ and $R^5=-(CH_2)_3-$, $R^6=$t-Bu (Compound 52)]:

IR $\nu_{max}^{neat}$cm$^{-1}$: 1770, 1735, 1705, 1640.

$^1$H-NMR δ ppm(CDCl$_3$): 4.92–4.24(m, 2H), 3.84–3.38(m, 3H), 3.09(m, 2H), 2.44–1.06(m, 32H), 1.43(s, 9H), 1.41(s, 9H), 0.87(t, 6H).

Mass(EI) m/z: 651(M+).

[α]$_D$: −50.7° (C=0.5, methanol).

Example 57

$N^\alpha$-[1-oxa-2-oxospiro[4.6]undecan-3(S)-yl]-$N^\epsilon$-t-butyoxycarbonyl-(S)-lysyl-(S)-proline t-butyl ester [in the formula (I), $R^1$ and $R_2=-(CH_2)_6-$, $R^3=-(CH_2)_4NHCOO$-t-Bu, $R^4$ and $R^5=-(CH_2)_3-$, $R^6=$t-Bu (Compound 53)]:

IR $\nu_{max}^{neat}$cm$^{-1}$: 1770, 1735, 1700, 1640.

$^1$H-NMR δ ppm(CDCl$_3$): 4.90–4.20(m, 2H), 3.86–3.38(m, 3H), 3.09(m, 2H), 2.48–1.20(m, 24H), 1.43(s, 9H), 1.41(s, 9H).

Mass(EI) m/z: 565.

[α]$_D$: −66.7° (C=0.5, methanol).

Examples 58-60

Compounds 51, 52 and 53 obtained in Examples 55–57 were each added with a 4N HCl-dioxane solution. Thereafter, a reaction and treatments were conducted in the same manner as in Example 40 so that the dihydrochlorides of Compounds 54, 55 and 56, given below in Examples 58–60, were each obtained as colorless crystals.

Example 58

Dihydrochloride of $N^\alpha$-[2-oxo-5,5-dipentyl-3(S)-tetrahydrofuranyl]-(S)-lysyl-(S)-proline [in the formula (I), $R^1=-(CH_2)_4CH_3$, $R^2=-(CH_2)_4CH_3$, $R^3=-(CH_2)_4NH_2$, $R^4$ and $R^5=-(CH_2)_3-$, $R^6=$H (Compound 54)]:

Melting point: 156°–158° C.

IR $\nu_{max}^{KBr}$cm$^{-1}$: 1770, 1720, 1645.

$^1$H-NMR δ ppm(DMSO-d$_6$): 8.06(br, 2H), 4.70–4.08(m, 3H), 3.58(m, 2H), 2.87–2.56(m, 3H), 2.36–1.08(m, 27H), 0.86(t, 6H).

Mass(FAB) m/z: 468[(M+H−2HCl)+].

[α]$_D$: −48.5° (C=0.5, methanol).

Example 59

Dihydrochloride of $N^\alpha$-[2-oxo-5,5-dihexyl-3(S)-tetrahydrofuranyl]-(S)-lysyl-(S)-proline [in the formula (I), $R^1=-(CH_2)_5CH_3$, $R^2=-(CH_2)_5CH_3$, $R^3=-(CH_2)_4NH_2$, $R^4$ and $R^5=-(CH_2)_3-$, $R^6=$H (Compound 55)]:

Melting point: 132°–135° C.

IR $\nu_{max}^{KBr}$cm$^{-1}$: 1770, 1715, 1640.

$^1$H-NMR δ ppm(DMSO-d$_6$): 8.08(br, 2H), 4.73–4.08(m, 3H), 3.61(m, 2H), 2.90–2.54(m, 3H), 2.36–1.04(m, 31H), 0.86(t, 6H).

Mass(FAB) m/z: 496[(M+H−2HCl)+].

[α]$_D$: −46.9° (C=0.5, methanol).

Example 60

Dihydrochloride of $N^\alpha$-[1-oxa-2-oxospiro[4.6]-undecan-3(S)-yl]-(S)-lysyl-(S)-proline [in the formula (I), $R^1$ and $R_2=-(CH_2)_6-$, $R^3=-(CH_2)_4NH_2$, $R^4$ and $R^5=-(CH_2)_3-$, $R^6=$H (Compound 56)]:

Melting point: 204°–206° C.

IR $\nu_{max}^{KBr}$cm$^{-1}$: 1770, 1720, 1640.

$^1$H-NMR δ ppm(DMSO-d$_6$): 8.06(br, 2H), 4.84–4.06(m, 3H), 3.60(m, 2H), 2.87–2.57(m, 3H), 2.32–1.16(m, 23H).

Mass(FAB) m/z: 410[(M+H−2HCl)+].

[α]$_D$: −55.0° (C=0.5, methanol).

Having now fully described the invention, it will be apparent to one of ordinary skill in the art that many changes and modifications can be made thereto without departing from the spirit or scope of the invention as set forth herein.

What is claimed is:

1. A γ-butyrolactone derivative represented by formula (I)

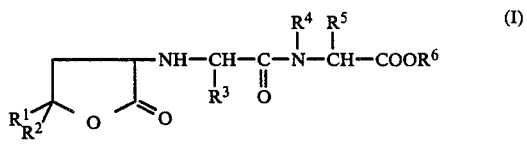

wherein $R^1$ and $R^2$ may be the same or different and each individually is a hydrogen atom or a straight-chain or branched chain alkyl group, or $R^1$ and $R^2$ are bonded together thereby forming an alkylene group of 2–6 carbon atoms, $R^3$ is hydrogen or a lower alkyl, aralkyl, amino lower alkyl or lower alkoxycarbonylamino lower alkyl group, $R^4$ is a lower alkyl, cycloalkyl or aralkyl group, $R^5$ is hydrogen or a lower alkyl group, or $R^4$ and $R^5$ are bonded together to form an alkylene group having from 2–4 carbon atoms, and $R^6$ is hydrogen or a lower alkyl or aralkyl group; or a pharmacologically acceptable salt thereof.

2. A gamma-butyrolactone derivative represented by the formula:

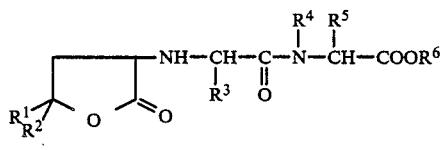 (I)

wherein $R^1$ and $R^2$ may be the same or different and each individually is hydrogen or a straight-chain or branched alkyl; $R^3$ is hydrogen, lower alkyl, aralkyl, amino lower alkyl or lower alkoxycarbonylamino lower alkyl; $R^4$ and $R^5$ are bonded together thereby forming an alkylene group of 2-4 carbon atoms; and $R^6$ is hydrogen, lower alkyl or aralkyl, or a pharmaceutically acceptable salt thereof.

3. The gamma-butyrolactone derivative of claim 2, wherein $R^1$ is $-(CH_2)_4CH_3$, $R^2$ is hydrogen, $R^3$ is $-(CH_2)_4NH_2$, $R^4$ and $R^5$ together are $-(CH_2)_3-$ and $R^6$ is hydrogen.

* * * * *